US011266620B2

(12) United States Patent
Jalan et al.

(10) Patent No.: US 11,266,620 B2
(45) Date of Patent: Mar. 8, 2022

(54) TREATMENT OF PORTAL HYPERTENSION AND RESTORATION OF LIVER FUNCTION USING L-ORNITHINE PHENYLACETATE

(71) Applicants: UCL BUSINESS PLC, London (GB); Ocera Therapeutics, Inc., Redwood City, CA (US)

(72) Inventors: Rajiv Jalan, Chislehurst (GB); Keith Anderson, San Diego, CA (US)

(73) Assignees: UCL Business Ltd, London (GB); Ocera Therapeutics, Inc., Hazelwood, MO (US)

(*) Notice: Subject to any disclaimer, the term of this patent is extended or adjusted under 35 U.S.C. 154(b) by 0 days.

(21) Appl. No.: 15/817,847

(22) Filed: Nov. 20, 2017

(65) Prior Publication Data

US 2018/0161293 A1 Jun. 14, 2018

Related U.S. Application Data

(63) Continuation of application No. 13/375,463, filed as application No. PCT/US2010/037838 on Jun. 8, 2010, now abandoned.

(60) Provisional application No. 61/296,377, filed on Jan. 19, 2010, provisional application No. 61/240,748, filed on Sep. 9, 2009, provisional application No. 61/185,158, filed on Jun. 8, 2009.

(51) Int. Cl.
| A61K 31/198 | (2006.01) |
| A61P 1/16 | (2006.01) |
| A61K 31/192 | (2006.01) |
| A61K 31/195 | (2006.01) |
| A61P 29/00 | (2006.01) |
| A61K 31/19 | (2006.01) |

(52) U.S. Cl.
CPC ............ *A61K 31/198* (2013.01); *A61K 31/19* (2013.01); *A61K 31/192* (2013.01); *A61K 31/195* (2013.01); *A61P 29/00* (2018.01)

(58) Field of Classification Search
CPC ....... A61P 1/16; A61K 31/198; A61K 2300/00
See application file for complete search history.

(56) References Cited

U.S. PATENT DOCUMENTS

| 3,950,529 A | 4/1976 | Fischer et al. |
| 4,100,293 A | 7/1978 | Walser |
| 4,228,099 A | 10/1980 | Walser |
| 4,284,647 A | 8/1981 | Brusilow et al. |
| 4,320,146 A | 3/1982 | Walser |
| 4,352,814 A | 10/1982 | Walser |
| 4,457,942 A | 7/1984 | Brusilow et al. |
| 4,857,555 A | 8/1989 | Smith et al. |
| 5,139,981 A | 8/1992 | Kurland |
| 5,194,625 A | 3/1993 | Tanabe et al. |
| 5,405,761 A | 4/1995 | Makryaleas et al. |
| 5,571,783 A | 11/1996 | Montagne et al. |
| 5,591,613 A | 1/1997 | Makryaleas et al. |
| 5,741,524 A | 4/1998 | Staniforth et al. |
| 5,767,086 A | 6/1998 | Kauvar et al. |
| 6,083,953 A | 6/2000 | Nestor et al. |
| 6,258,849 B1 | 7/2001 | Burzynski |
| 6,451,340 B1 | 9/2002 | Arimilli et al. |
| 6,503,530 B1 | 1/2003 | Kang et al. |
| 6,514,953 B1 | 2/2003 | Armitage et al. |
| 6,768,024 B1 | 7/2004 | Watson-Straughan et al. |
| 6,943,192 B2 | 9/2005 | Burzynski |
| 8,173,706 B2 | 5/2012 | Anderson et al. |
| 8,389,576 B2 | 3/2013 | Jalan et al. |
| 8,492,439 B2 | 7/2013 | Anderson et al. |
| 8,785,498 B2 | 7/2014 | Anderson et al. |
| 8,946,473 B2 | 2/2015 | Anderson et al. |
| 9,034,925 B2 | 5/2015 | Anderson et al. |
| 9,260,379 B2 | 2/2016 | Anderson et al. |
| 9,566,257 B2 | 2/2017 | Jalan et al. |
| 9,604,909 B2 | 3/2017 | Anderson et al. |
| 10,039,735 B2 | 8/2018 | Jalan et al. |
| 10,173,964 B2 | 1/2019 | Anderson et al. |
| 10,525,029 B2 | 1/2020 | Jalan et al. |
| 10,550,069 B2 | 2/2020 | Anderson et al. |
| 10,610,506 B2 | 4/2020 | Jalan et al. |
| 10,835,506 B2 | 11/2020 | Rose et al. |
| 2003/0105104 A1 | 6/2003 | Burzynski |
| 2003/0195255 A1 | 10/2003 | Summar |
| 2004/0024056 A1 | 2/2004 | Gu et al. |
| 2004/0152784 A1 | 8/2004 | March |
| 2004/0229948 A1 | 11/2004 | Summar et al. |
| 2005/0059150 A1 | 3/2005 | Guarino et al. |
| 2005/0182064 A1 | 8/2005 | Burzynski |
| 2006/0045912 A1 | 3/2006 | Truog |
| 2008/0119554 A1 | 5/2008 | Jalan et al. |
| 2008/0206324 A1 | 8/2008 | Gryczke et al. |
| 2010/0280119 A1 | 11/2010 | Anderson et al. |
| 2012/0157526 A1 | 6/2012 | Jalan et al. |
| 2012/0208885 A1 | 8/2012 | Anderson et al. |
| 2012/0259016 A1 | 10/2012 | Jalan et al. |

(Continued)

FOREIGN PATENT DOCUMENTS

| AU | 2014250643 A1 | 11/2014 |
| AU | 2015221466 A1 | 9/2015 |
| CA | 2763894 | 1/2011 |
| CA | 2813563 | 4/2012 |
| CN | 1383815 A | 12/2002 |
| CN | 101010087 A | 8/2007 |
| CN | 101102816 A | 1/2008 |
| CN | 101626769 A | 1/2010 |
| CN | 102421432 A | 4/2012 |
| CN | 103705490 A | 4/2014 |

(Continued)

OTHER PUBLICATIONS

Abraldes et al., "Hemodynamic Response to Pharmacological Treatment of Portal Hypertension and Long-Term Prognosis of Cirrhosis", Hepatol. 2003, 37:902-908.

(Continued)

*Primary Examiner* — Theodore R. Howell
(74) *Attorney, Agent, or Firm* — Knobbe, Martens, Olson & Bear, LLP

(57) ABSTRACT

Disclosed herein are methods of treating and/or preventing portal hypertension and/or restoring liver function using L-ornithine phenylacetate.

17 Claims, 8 Drawing Sheets

(56) References Cited

U.S. PATENT DOCUMENTS

| | | |
|---|---|---|
| 2013/0211135 A1 | 8/2013 | Anderson et al. |
| 2013/0296429 A1 | 11/2013 | Anderson et al. |
| 2014/0142186 A1 | 5/2014 | Scharschmidt et al. |
| 2014/0288327 A1 | 9/2014 | Anderson et al. |
| 2015/0133684 A1 | 5/2015 | Anderson et al. |
| 2015/0251990 A1 | 9/2015 | Anderson et al. |
| 2016/0338982 A1 | 11/2016 | Ruettimann et al. |
| 2017/0135973 A1 | 5/2017 | Wang et al. |
| 2017/0189364 A1 | 7/2017 | Jalan et al. |
| 2018/0044281 A1 | 2/2018 | Anderson et al. |
| 2018/0221320 A1 | 8/2018 | Rose et al. |
| 2018/0319736 A1 | 11/2018 | Anderson et al. |
| 2019/0070142 A1 | 3/2019 | Jalan et al. |
| 2020/0206174 A1 | 7/2020 | Rose et al. |
| 2020/0206175 A1 | 7/2020 | Jalan et al. |
| 2020/0239406 A1 | 7/2020 | Anderson et al. |

FOREIGN PATENT DOCUMENTS

| | | |
|---|---|---|
| EP | 1 179 347 A1 | 2/2002 |
| EP | 1 334 722 A1 | 8/2003 |
| EP | 1 374 863 A1 | 1/2004 |
| EP | 1 541 141 A1 | 6/2005 |
| FR | 2113774 A1 | 6/1972 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | 54-163518 A | 12/1979 |
| JP | H02-178256 A | 7/1990 |
| JP | 5-221858 A | 8/1993 |
| JP | 3273578 | 4/2002 |
| JP | 2004-517134 A | 6/2004 |
| JP | 2008-521784 | 6/2008 |
| JP | 2011-236160 | 11/2011 |
| MX | PA03009902 A | 3/2005 |
| WO | WO 85/004805 | 11/1985 |
| WO | WO 1987/005297 | 9/1987 |
| WO | WO 97/030167 | 8/1997 |
| WO | WO 00/071151 | 11/2000 |
| WO | WO 02/034255 | 5/2002 |
| WO | WO 02/074302 | 9/2002 |
| WO | WO 03/037378 | 5/2003 |
| WO | WO 03/045372 | 6/2003 |
| WO | WO 03/086074 | 10/2003 |
| WO | WO 2004/019928 | 3/2004 |
| WO | WO 2005/053607 | 6/2005 |
| WO | WO 2005/082023 | 9/2005 |
| WO | WO 2006/056794 | 6/2006 |
| WO | WO 2006/059237 | 6/2006 |
| WO | WO 2007/077995 | 7/2007 |
| WO | WO 2009/149196 | 12/2009 |
| WO | WO 2010/115055 | 10/2010 |
| WO | WO 2010/144498 | 12/2010 |
| WO | WO 2012/048043 | 4/2012 |
| WO | WO 2014/081977 | 5/2014 |
| WO | WO 2016/172112 | 10/2016 |

OTHER PUBLICATIONS

Aggarwal et al., "Predictors of Mortality and Resource Utilization in Cirrhotic Patients Admitted to the Medical ICU", Chest, 2001, vol. 119, Issue 5, pp. 1489-1497.

Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.

Albrecht et al., "Increase of the brain uptake index for L-ornithine in rats with hepatic encephalopathy", Neuro report., 1994, vol. 5, Issue 6, pp. 671-673.

Al-Hassnan et al., "The relationship of plasma glutamine to ammonium and of glycine to acid-base balance in propionic acidaemia", J. Inherit. Metab. Dis., 2003, vol. 26, pp. 89-91.

Als-Nielsen, Bodil, et al., Non-Absorbable Disaccharides for Hepatic Encephyalopathy: Systematic Review of Randomised Trials, BMJ, 2004, p. 1-6.

Anadiotis et al., "Ornithine transcarbamylase deficiency and pancreatitis", J Pediatr, 2001, vol. 138, pp. 123-124.

Anonymous, Sodium phenylbutyrate for urea cycle enzyme deficiencies. [No authors listed], Med Lett Drugs Ther., Nov. 1996, 38(988): 105-106.

Bachmann et al., "Ammonia toxicity to the brain and creatine", Molecular Genetics and Metabolism, 2004, vol. 81, pp. S52-S57.

Balata et al., "Induced hyperammonemia alters neuropsychology, brain MR spectroscopy and magnetization transfer in cirrhosis,", Hepatology, 2003, vol. 4, Issue 37, pp. 931-939.

Batshaw et al., "Alternative pathway therapy for urea cycle disorders: twenty years later", J Pediatr, 2001, vol. 138, Issue 1, pp. S46-S55.

Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.

Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.

Berg et al., "Pharmacokinetics and cerebrospinal fluid penetration of pheylacetate and phenylbutyrate in the non-human primate", Cancer Chemother Pharmacol. (May 2001) 47(5): 385-390. Abstract Only.

Berge et al., "Pharmaceutical Salts", J Pharm Sci, 1977, vol. 66, pp. 1-19.

Berry et al., "Long-term management of patients with urea cycle disorders", J Pediatri, 2001, vol. 138, Issue 1, pp. S56-S61.

Bighley et al., "Salt Forms of Drugs and Absorption" in Encyclopedia of Pharmaceutical Technology, Eds. J. Swarbrick and J.C. Boylan, vol. 13, Marcel Dekker, Inc., New York, (1996), pp. 453-499.

Blei, Andres T., et al., Pathophysiology of Cerebral Edema in Fulminant Hepatic Failure, Journal of Hepatology, 1999, p. 771-776, vol. 31, Denmark.

Bleichner, et al., "Frequency of infections in cirrhotic patients presenting with acute gastrointestinal haemorrhage", British Journal of Surgery, 1986, vol. 73, Issue 9, pp. 724-726.

Bongers et al., "Exogenous glutamine: the clinical evidence,", Crit Care Med., 2007, vol. 9 Suppl, Issue 35, pp. S545-S552.

Braga et al., "Crystal Polymorphism and Multiple Crystal Forms", Struct Bond (2009) 132: 25-50 [pub online Feb. 25, 2009].

Briggs et al., Biochem J, 1976, vol. 160, pp. 205-209.

Bruha et al. Effect of carvedilol on portal hypertension depends on the degree of endothelial activation and inflammatory changes, Scand. J. Gastroenterol., 41(12):1454-1463 (2006).

Brunquell et al., "Electroencephalographic findings in ornithine transcarbamylase deficiency", J Child Neurol, 1999, vol. 14, Issue 8, pp. 533-536.

Brusilow et al., "Amino acid acylation: A mechanism of nitrogen excretion in inborn errors of urea synthesis", Science, 1980, vol. 207, pp. 659-661.

Brusilow et al., "Treatment of episodic hyperammonemia in children with inborn errors of urea synthesis", The New England Journal of Medicine, 1984, vol. 310, Issue 25, pp. 1630-1634.

Burlina et al., "Long-term treatment with sodium phenylbutyrate in ornithine transcarbamylase-deficient patients", Molecular Genetics and Metabolism, 2001, vol. 72, pp. 351-355.

Butterworth, "Pathophysiology of hepatic encephalopathy: a new look at ammonia", Metab Brain Dis., 2002, vol. 17, Issue 4, pp. 221-227.

Byrn et al., "Pharmaceutical Solids: A Strategic Approach to Regulatory Considerations", Pharma Res. (1995) 12(7): 945-954.

Caira, M.R., "Crystalline Polymorphism of Organic Compounds", Topic in Current Chemistry (1998) 198: 163-208.

(56) References Cited

OTHER PUBLICATIONS

Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan.
Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chawla et al., "Challenges in Polymorphism of Pharmaceuticals", CRIPS (Mar. 2004) 5(1): 9-12.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
ClinicalTrails.gov; William Lee, Med. Uni. S.C.; "Safety Study of Ornithine Phenylacetate to Treat Patients with Acute Liver Failure (STOP-ALF)", ID #NCT01548690; Feb. 2012; 7 pages.
Damink et al., Stimulated Liver and Muscle Protein Synthesis by Intravenous Isoleucine Supplementation During a Simulated Variceal Bleed in Patients with Cirrhosis of the Liver, Hepatology, Oct. 2001, AASLD Abstracts #50.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section Ch, Week 200331, Derwent Publications Ltd., London, GB; XP002364873 & CN 1383815 A (Liu W), Dec. 11, 2002 (Abstract Only).
Davies, et al., "L-ornithine and phenylacetate synergistically produce sustained reduction in ammonia and brain water in cirrhotic rats", Hepatology (Jul. 2009) 50(1): 155-164.
Declaration of Non-Establishment of International Search Report and Written Opinion dated Feb. 28, 2011 for International Application No. PCT/US2010/037838, filed Jun. 8, 2010.
Dejong et al., "Altered glutamine metabolism in rat portal drained viscera and hindquarter during hyperammonemia", Gastroenterology, 1992, vol. 103, Issue 3, pp. 936-948.
Del Rosario et al., Hyperammonemic encephalopathy, J Clin Gastroenterol, 1997, vol. 25, Issue 4, pp. 682-684.
Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dunitz et al., "Disappearing Polymorphs", Acc Chem. Res. (1995) 28: 193-200.
Enns et al., "Survival after treatment with phenylacetate and benzoate for urea-cycle disorders,", N Engl J Med., 2007, vol. 22, Issue 356, pp. 2282-2292.
Fabbri, Andrea et al., Unresponsiveness of Hepatic Nitrogen Metabolism to Glucagon Infusion in Patients with Cirrhosis: Dependence on Liver Cell Failure, Hepatology, 1993, vol. 18, No. 1, pp. 28-35.
Garcia-Tsao, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.
Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Grant, D.J.W., "Theory and Origin of Polymorphism" Chapter 1 from Polymorphism in Pharmaceutical Solids, Brittain, Harry G. [Ed.]; Marcel Dekker, Inc., (1999) pp. 1-11.
Greensteine et al., Arch Biochem Biophys, 1956, vol. 64, pp. 342-354.
Grossi et al., "Amino acids mixtures in prevention of acute ammonia intoxication in dogs", Arch Surg, 1967, vol. 94, pp. 261-266.
Guillory, J.K., "Generation of Polymorphs, Hydrates, Solvates, and Amorphous" Chapter 5 from Polymorphism in Pharmaceutical Solids, Brittain, Harry G. [Ed.]; Marcel Dekker, Inc., (1999) pp. 183-226.
Häberle et al., Hyperammonämie: Ursachen, Diagnostik, Therapie, Dtsch Med Wochenschr, 2004, pp. 1430-1433, vol. 129.
Hamberg, Ole et al., Effects of an Increase in Protein Intake on Hepatic Efficacy for Urea Synthesis in Healthy Subjects and in Patients with Cirrhosis, Journal of Hepatology, 1992, pp. 237-243, Elsevier Science Publishers B.V.
Harrison's Principles of Internal Medicine (16th Edition) 2005, pp. 1863-1869.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Hirayama et al., [Eds], "Organic compound crystal produced handbook—Principles and know-how", Maruzen Co., Ltd., Japan; (Jul. 2008), pp. 17-23, 37-40, 45-51 and 57-65; 31 pages.
Honda et al., "Successful treatment of severe hyperammonemia using sodium phenylacetate powder prepared in hospital pharmacy", Biol. Pharm. Bull., Sep. 2002, 25(9): 1244-1246.
Hopkins Medicine (http://www.hopkinsmedicine.org/gastroenterology_hepatology/_pdfs/liver/portal_hypertension.pdf, accessed Jun. 22, 2016).
Hursthouse et al., "Why Do Organic Compounds Crystallise Well or Badly or Ever so Slowly? Why Is Crystallisation Nevertheless Such a Good Purification Technique?" Organic Process Research & Development, (2009) 13:1231-1240.
Igarashi et al., "Determination of ornithine conjugates of some carboxylic acids in birds by high-performance liquid chromatography", Chem Pharm Bull, 1992, vol. 40, Issue 8, pp. 2196-2198.
Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.
Iyer et al., "Mouse model for human arginase deficiency", Mol Cell Biol., 2002, vol. 22, Issue 13, pp. 4491-4498.
Jalan et al. L-Ornithine phenylacetate (OP): A novel treatment for hyperamonen and hepatic encephalopathy. Medical Hypotheses, 69:1064-1069 (2007).
Jalan et al., "Acute-on-chronic liver failure: pathophysiological basis of therapeutic options", Blood Purif, 2002, vol. 20, pp. 252-261.
Jalan et al., "Moderate hypothermia in patients with acute liver failure and uncontrolled intracranial hypertension,", Gastroenterology, 2004, vol. 5, Issue 127, pp. 1338-1346.
Jalan et al., "The molecular pathogenesis of hepatic encephalopathy", The International Journal of Biochemistry & Cell Biology, 2003, vol. 35, pp. 1175-1181.
Jalan et al., L-Ornithine Phenylacetate (OP): A Novel Treatment for Hyperammonemia and Hepatic Encephalopathy, Medical Hypotheses, 2007, p. 1064-1069, vol. 69, Elsevier Ltd.

(56) References Cited

OTHER PUBLICATIONS

Jalan, Intracranial Hypertension in Acute Liver Failure: Pathophysiological Basis of Rational Management, Seminars in Liver Disease, 2003, p. 271-282, vol. 23, No. 3, Thieme Medical Publisheres, Inc., New York, NY, USA.

Jalan et al, Treatment of Hyperammonemia in Liver Failure: A Tale of Two Enzymes, Gastroenterology, 2009, p. 2048-2051, vol. 1236.

James et al., "The conjugation of phenylacetic acid in man, sub-human primates and some non-primate species", Proc R Soc Lond B., 1972, vol. 182, pp. 25-35.

Jeyamani et al., Hepatitis E virus and acute-on-chronic liver failure,, Indian J Gastroentero., 2004, vol. 23, Issue 2, pp. 45-46.

Jiang, et al., "L-Ornithine-L-aspartate in the management of hepatic encephalopathy: A meta-analysis", Journal of Gastroenterology and Hepatology, 2008, pp. 1-6.

Kaiser et al., Ammonia and Glutamine Metabolism in Human Liver Slices: New Aspects on the Pathogenesis of Hyperammonaemia in Chronic Liver Disease, European journal of Clinical Investigation, 1988, vol. 18, pp. 535-542.

Kasumov et al., "New secondary metabolites of phenylbutyrate in humans and rats", Drug Metab Dispos., 2004, vol. 32, Issue 1, pp. 10-19.

Katayama, "Ammonia metabolism and hepatic encephalopathy", Hep. Research, 2004, vol. 30, Issue 1, pp. S71-S78.

Khan, et al., Frequency of Spontaneous Bacterial Peritonitis in Cirrhotic Patients with Ascites Due to Hepatitis C Virus and Efficacy of Cirpofloxacin in its Treatment, Gomal Journal of Medical Sciences, Jul.-Dec. 2009, pp. 149-154, vol. 7, No. 2.

Khanna et al., "Non-cirrhotic portal hypertension—Diagnosis and management", J. Hepatol., Feb. 2014, 60(2): 421-441.

Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.

Kojima et al., "Effective Solid Form Selection for the Pharmaceutical Development", J Pharma Science Tech. (Sep. 2008) 68(5): 344-349.

Larsen et al., "Alternative Pathway Therapy for Hyperammonemia in Liver Failure"; Hepatology, Jul. 2009, 50(1): 3-5.

Lee et al., Acute Liver Failure: Summary of a Workshop, Hepatology, Apr. 2008, p. 1401-1415, vol. 47, No. 4.

Lee, W. M., Acetaminophen-Related Acute Liver Failure in the United States, Hepatology Research, 2008, p. S3-S8, vol. 38, Suppl. 1, The Japan Society of Hepatology.

Linderoth et al., "Short-term prognosis of community-acquired bacteremia in patients with liver cirrhosis or alcoholism: A population-based cohort study,", Alcohol Clin Exp Res., 2006, Issue 30, pp. 636-641.

Lopez-Talavera et al. Thalidomide inhibits tumor necrosis factor alpha, decreases nitric oxide synthesis, and ameliorates the hyperdynamic circulatory syndrome in portal-hypertensive rats, Hepatology, 23(6):1616-1621 (1996).

Lukkarinen, M. et al., Oral Supplementation Corrects Plasma Lysine Concentrations in Lysinuric Protein Intolerance, Metabolism, Jul. 2003, pp. 935-938, vol. 52, No. 7, Elsevier Inc.

Macarthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.

Maestri et al., "Long-term treatment of girls with ornithine transcarbamylase deficiency", N Engl J Med., 1996, vol. 335, Issue 12, pp. 855-859.

Maestri et al., "Prospective treatment of urea cycle disorders", J Pediatr., 1991, vol. 119, Issue 6, pp. 923-928.

Maev I.V. Primenenie preparata L-ornitin-L-aspartata v kompleksnoy terapii pechyonochnoy entsefalopatii u bolnykh tsirrozom pecheni. Rossiyskiy zhurnal gastroenterologii, gepatologii, koloproktologii, 2002, No. 6, pp. 60-66 (English translation thereof is also enclosed).

Maier, "Therapie der hepatischen Enzephalopathie", Dtsch med Wschr, 1988, vol. 113, pp. 1886-1889.

Maier, K. P. et al., Originalien Activities of Urea-Cycle Enzymes in Chronic Liver Disease, Klinische-Wochenschrift, 1979, vol. 67, pp. 661-665, Springer-Verlag.

Matsuoka et al., "Advanced Crystallization Technology of Organic Materials—Control of Size, Morphology, Polymorph and Purity", Pharm Tech, Japan (May 2003) 19(6): 91(955)-101(965).

Meijer et al. Nitrogen Metabolism and Ornithine Cycle Function, Physiological Reviews, Jul. 1990, vol. 70, No. 3, pp. 701-748, The American Physiological Society.

Mendenhall et al., "A new therapy for portal systemic encephalopathy", The American Journal of Gastroenterology, 1986, vol. 81, Issue 7, pp. 540-543.

Mihm et al., "Effect of L-ornithine-L-aspartate (LOLA) on neurometabolites in hepatic encephalopathy (HE)", Hepatology, 2001, vol. 34, Issue 4, pp. 543A.

Mizock et al., "Septic Encephalopathy—Evidence for altered phenylalanine metabolism and comparison with hepatic encephalopathy", Arch Intern Med, 1990, vol. 150, pp. 443-449.

Mizock, MD, FACP, Nutritional Support in Hepatic Encephalopathy, Nutrition, 1999, pp. 220-228, vol. 15, No. 3, Elsevier Science Inc.

Mizutani et al., "Hyperargininemia: Clinical course and treatment with sodium benzoate and phenylacetic acid", Brain Dev., 1983, vol. 5, Issue 6, pp. 555-563.

Moinard et al., "Effects of Ornithine 2-Oxoglutarateon Neutrophils in Stressed Rates: Evidence for the Involvement of Nitric Oxide and Polyamines", Clin Sci, 2002, vol. 102, Issue 3, pp. 287-295, London, England.

Mookerjee et al., "Neutrophil dysfunction in alcoholilc hepatitis superimposed on cirrhosis is reversible and predicts the outcome,", Hepatology, 2007, vol. 3, Issue 46, pp. 831-840.

Mouille et al., Am J Gasteroenterol, 2004, vol. 287, pp. 344-351.

Nance et al., "Ammonia production in germ-free Eck fistula dogs", Surgery, 1971, vol. 70, Issue 2, pp. 169-174.

Navasa et al., "Bacterial infections in liver cirrhosis,", Ital J Gastroenterol Hepatol., 1999, vol. 7, Issue 31, pp. 616-625.

Newsholme et al., "Glutamine metabolism by lymphocytes, macrophages, and neutrophils: its importance in health and disease,", J Nutr Biochem., 1999, vol. 6, Issue 10, pp. 316-324.

Newsholme, "Why is L-glutamine metabolism important to cells of the immune system in health, postinjury, surgery or infection?", J Nutr., 2001, vol. 9 Suppl, Issue 131, pp. 2515S-2522S.

Olde Damink et al., "Decreased plasma and tissue isoleucine levels after simulated gastrointestinal bleeding by blood gavages in chronic portacaval shunted rats", Gut, 1997, vol. 40, pp. 418-424.

Olde Damink et al., "Interorgan ammonia and amino acid metabolism in metabolically stable patients with cirrhosis and a TIPSS", Hepatology, 2002, vol. 36, Issue 5, pp. 1163-1171.

Olde Damink et al., "Interorgan ammonia metabolism in liver failure", [not known], 2002, vol. 41, pp. 177-188.

Olde Damink et al., "The kidney plays a major role in the hyperammonemia seen after simulated or actual GI bleeding in patients with cirrhosis", [not known], 2003, vol. 37, pp. 1277-1285.

Pauwels et al., "Systemic antibiotic prophylaxis after gastrointestinal hemorrhage in cirrhotic patients with a high risk of infection", Hepatology, 1996, vol. 24, Issue 4, pp. 802-806.

Petrowski et al., "Pharmacologic amino acid acylation in the acute hyperammonemia of propionic acidemia", Journal of Neurogenetics, 1987, vol. 4, pp. 87-96.

Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.

Praphanphoj et al., "Three cases of intravenous sodium benzoate and sodium phenylacetate toxicity occurring in the treatment of acute hyperammonaemia", J Inherit Metab Dis., 2000, vol. 23, pp. 129-136.

Rajkovic et al., "Mechanisms of abnormalities in host defences against bacterial infection in liver disease,", Clin Sci. (Lond.), 1985, vol. 3, Issue 68, pp. 247-253, London.

Ramaswamy et al., "Mouse model for human arginase deficiency", Mol Cell Biol., Jul. 2002, vol. 22, Issue 13, pp. 4491-4498.

(56) References Cited

OTHER PUBLICATIONS

Rees et al., "Effect of L-Ornithine-L-Aspartate on patients with and without TIPS undergoing glutamine challenge: a double blind, placebo controlled trial", Gut, 2000, vol. 47, pp. 571-574.
Riordan et al., "Treatment of hepatic encephalopathy", Curr Concepts, 1997, vol. 337, Issue 7, pp. 473-479.
Rogers, Q. R. et al., Deficiency of Pyrroline-5-Carboxylate Synthase in the Intestinal Mucosa of the Cat, The Journal of Nutrition, 1985, pp. 146-150, vol. 115, No. 1, American Institution of Nutrition.
Romero-Gómez et al., "Intestinal glutaminase activity is increased in liver cirrhosis and correlates with minimal hepatic encephalopathy", Journal of Hepatology, 2004, vol. 41, pp. 49-54.
Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.
Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.
Rudman, et al., Maximal Rates of Excretion and Synthesis of Urea in Normal and Cirrhotic Subjects, The Journal of Clinical Investigation, Sep. 1973, vol. 52, pp. 2241-2249.
Rukmini Devi et al., "Region-specific changes in CNS muscarinic acetylcholine receptors in a rat model of hyperammonemia", Biochem Pharmacol., 1998, vol. 56, Issue 2, pp. 237-241.
Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.
Sanyal, A. J., Prediction of Variceal Hemorrhage in Patients with Cirrhosis, UpToDate, Inc., Website (www.uptodate.com), Jan. 2010, UpToDate.
Sarhan et al., "Effects of inhibition of ornithine aminotransferase on thioactamide-induced hepatogenic encephalopathy", Neurochem Res., 1993, vol. 18, Issue 4, pp. 539-549.
Scaglia et al., "Effect of alternative pathway therapy on branched chain amino acid metabolism in urea cycle disorder patients", Mol Genet Metabolism, 2004, vol. 81, pp. S79-S85.
Schouten et al. "Idiopathic noncirrhotic portal hypertension", Hepatology, Sep. 2011; 54(3):1071-1081.
Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.
Seiler et al., "Ornithine aminotransferase activity, liver ornithine concentration and acute ammonia intoxication", Life Sciences, 1989, vol. 45, Issue 11, pp. 1009-1020.
Seiler, "Ornithine aminotransferase, a potential target for the treatment of hyperammonemias", Curr Drug Targets., Sep. 2000, vol. 1, Issue 2, pp. 119-153.
Sen et al., "The pathophysiological basis of acute-on-chronic liver failure", Liver, 2002, vol. 22, Issue Suppl. 2, pp. 5-13.
Shangraw et al., Effect of Liver Disease and Transplantation on Urea Synthesis in Humans: Relationship to Acid-Base Status, Am J Physiol Gastrointest Liver Physiol, 1999, vol. 276, pp. 1145-1152.
Shawcross et al., "Ammonia impairs neutrophil phagocytic function in liver disease,", Hepatology, 2008, vol. 4, Issue 48, pp. 1202-1212.
Shawcross et al., "Dispelling myths in the teatment of hepatic encephalopathy,", Lancet, 2005, vol. 9457, Issue 365, pp. 431-433.
Shawcross et al., "Hyperammonemia impairs neutrophil function", Hepatology, 2005, vol. 42, pp. 537A.
Shriner, et al., "Recrystallization," in The Systematic Identification of Organic Compounds, John Wiley & Sons, Inc., New York, (1998), pp. 78-81.
Simell et al., "Waste nitrogen excretion via amino acid acylation: benzoate and phenylacetate in lysinuric protein intolerance", Pediatric Research, 1986, vol. 20, Issue 11, pp. 1117-1121.
Singaporean Search & Examination Report dated Nov. 5, 2013 for Application No. 201108982-8, filed Jun. 8, 2010.

Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.
Smith et al., "The treatment of inborn errors of the urea cycle", Nature, 1981, vol. 291, Issue 5814, pp. 378-380.
"Sodium phenylbutyrate for urea cycle enzyme deficiencies." [No authors listed], Med Lett Drugs Ther., Nov. 22, 1996, vol. 38, Issue 988, pp. 105-106.
Soláini et al., "Variations in the plasma concentration of ornithine, citrulline and arginine in acute experimental liver failure" [Article in Italian], Boll Soc Ital Biol Sper., 1981, vol. 57, Issue 7, pp. 705-710.
Stedman's Medical Dictionary (27th Edition, 2002).
Stewart, P. M., et al., Effects of Arginine-Free Meals on Ureagenesis in Cats, American Journal of Physiological, 1981, pp. E310-E315, vol. 241, No. 4, The American Physiological Society.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.
Suchy et al., Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat,", J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
TDRdata.com, results from query of "Spontaneous Bacterial Peritonitis" in the epidemiological and references databases at www.tdrdata.com, retrieved on Jul. 27, 2010, pp. 1-7.
Teran et al., "Primary prophylaxis of variceal bleeding in cirrhosis: A cost-effectiveness analysis", Gastroenter., 1997, vol. 112, Issue 2, pp. 473-482.
Trebick et al. Atorvastin lowers portal pressure in cirrhotic rats by inhibition of RhoA/Roh-kinase and activation of endothelial nitric oxide synthase, Hapatology, 46(1):242-253 (2007).
Tuchman, M., et al., Management of Inherited Disorders of Ureagenesis, The Endocrinologist, 2002, p. 99-109, vol. 12, No. 2.
Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.
Van Den Berg et al., "The effect of glutamine-enriched enteral nutrition on intestinal microflora in very low birth weight infants: a randomized controlled trial,", Clin Nutr., 2007, vol. 4, Issue 26, pp. 430-439.
Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.
Vogels et al., "L-ornithine vs L-ornithine-L-aspartate as a treatment for hyperammonemia-induced encephalopathy in rats", J Hepatology, 1997, vol. 26, Issue 1, pp. 174-182.
Wasmuth et al., "Patients with acute on chronic liver failure display 'sepsis-like' immune paralysis,", J Hepatol., 2005, vol. 2, Issue 42, pp. 195-201.
Wright et al., "773 Reduction in ammonia with L-ornithine, phenylacetate (OP) but not anti-TNF prevents LPS induced brain edema in bile-duct ligated cirrhotic rats," Journal of Hepatology, 50:S283 (2009).
Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology (2009) 50: S283.

(56) References Cited

OTHER PUBLICATIONS

Ytrebø et al., "Interorgan ammonia, glutamate, and glutamine trafficking in pigs with acute liver failure,", Am J Physiol Gastrointest Liver Physiol., 2006, vol. 3, Issue 291, pp. G373-G381.

Ytrebø et al., "L-Ornithine Phenylacetate Attenuates Increased Arterial and Extracellular Brain Ammonia and Prevents Intracranial Hypertension in Pigs with Acute Liver Failure", Hepatology (Jul. 2009) 50(1): 165-174.

Yudkoff et al., "In Vivo Nitrogen Metabolism in Ornithine Transcarbamylase Deficiency", J Clin. Invest, Nov. 1996, 98(9): 2167-2173.

Zetterman, Rowen K., MD, "Complications of Portal Hypertension: Hepatic Encephalopathy", Medscape (Jun. 2011) available online at www.medscape.com/viewarticle/744392; downloaded Dec. 3, 2014; 6 pages.

Zieve et al., "Ammonia toxicity: comparative protective effect of various arginine and ornithine derivatives, aspartate, benzoate, and carbamyl glutamate", Metabo Brain Dis., 1986, vol. 1, Issue 1, pp. 25-35.

Zieve et al., "Conditional deficiencies of ornithine or ornithine or arginine", J Am Coll Nutr., 1986, vol. 5, Issue 2, pp. 167-176.

European Examination Report dated Jan. 27, 2012 from EP Patent Application No. 09 013 613.6-2123.

European Examination Report dated Nov. 5, 2008 from EP patent application No. 05808837.8.

Extended European Search Report European Application No. 09013613.6, dated Jan. 15, 2010.

Extended Search Report for European Application No. 10014283.5, dated Mar. 10, 2011.

Office Communication dated Feb. 13, 2012, for European Application No. 10 014 283.5-2123.

Office Action dated Nov. 27, 2014 for Eurasian Application No. 201171396, filed Jun. 8, 2010.

Office Action dated Oct. 9, 2013 for Eurasian Application No. 201171396 filed Jun. 8, 2010.

Office Action dated Aug. 6, 2013 for European Application No. 10786721.0 filed Jun. 8, 2010.

Search Report dated Oct. 6, 2014 for European Application No. 14175859.9, filed Jun. 9, 2010.

Examination Report dated Jun. 21, 2012 in New Zealand Patent Application No. 596916 filed Jun. 8, 2010.

Extended European Search Report dated Oct. 31, 2012 for European Patent Application No. 10786721.0, filed Jun. 9, 2010.

Intellectual Property Office of Singapore (IPOS) Search Report and Written Opinion, dated Apr. 23, 2010, Singapore Patent Application No. 200907712-4.

Intellectual Property Office of Singapore, Examination Report for Singapore Patent Application No. 200907712-4, dated Jan. 21, 2011.

International Preliminary Report on Patentability dated May 30, 2007 during the prosecution of the International Application No. PCT/GB2005/004539.

International Search Report dated Feb. 8, 2006 during the prosecution of the International Application No. PCT/GB2005/004539.

International Search Report dated Jun. 3, 2010 during the prosecution of the International Application No. PCT/US2010/029708.GB.

Israel Office Action dated Oct. 2, 3014 for Application No. 216811, filed Jun. 8, 2010.

Israel Patent Office, Office Action for Israeli Patent Application No. 183401, dated Jan. 6, 2011 (English Translation Only).

Office Action dated Nov. 15, 2011 for Japanese Patent Application No. 2007-542118, (including English Translation).

Office Action dated May 15, 2014 for Mexican Application No. MX/a/2011/013129, filed Jun. 8, 2010.

Official Action for Mexican Patent Application No. MX/a/2007/006171, dated Oct. 2 010.

Examination Report dated Apr. 18, 2008 for New Zealand application No. 555870.

Examination Report dated Sep. 11, 2013 for New Zealand Application No. 615091 filed Sep. 5, 2013.

New Zealand Office Action dated Nov. 20, 2014 for NZ Application No. 615091, filed Sep. 5, 2013.

Office Action and Search Report dated Feb. 1, 2013 (and English translation thereof) for Chinese Patent Application No. 201080035200.0, filed June 8, 2010.

Office Action dated Jun. 24, 2016 for European Application No. 14175859.9, filed Jul. 4, 2014.

Office Action dated Apr. 21, 2016 for Korean Application No. 10-2012-7000293, filed Jun. 8, 2010.

Office Action dated Aug. 9, 2016 for Japanese Application No. 2015-098205, filed May 13, 2015.

Office Action dated Jan. 30, 2014 for Australian Application No. 2010258888, filed Jun. 8, 2010.

Office Action dated Jul. 1, 2016 for Australian Application No. 2014250643, filed Oct. 15, 2014.

Office Action dated Mar. 15, 2016 for Japanese Application No. 2015-163635, filed May 13, 2015.

Office Action dated May 10, 2016 for Canadian Application No. 2,764,587, filed Jun. 8, 2010.

Office Action dated May 5, 2016 for Chinese Application No. 201410350083.7, filed Jul. 22, 2014.

Office Action dated Nov. 14, 2013 for Mexican Application No. MX/a/2011/013129, filed Jun. 8, 2010.

Office Action dated Oct. 23, 2013 for Chinese Application No. 201080035200.0, filed Jun. 8, 2010.

Search Report dated Apr. 8, 2005 from GB patent application No. 0426142.6.

Search Report dated Jun. 25, 2012 in Eurasian Patent Application No. 201171396 filed Jun. 8, 2010.

Search Report dated Feb. 22, 2005 during the prosecution of the GB priority application No. 0426141.8.

Office Action dated Nov. 26, 2010 for Chinese Patent Application No. 200580046990.1.

Written Opinion for Singapore Application No. 201108982-8, dated Mar. 1, 2013.

Written Opinion of the International Search Authority dated Feb. 7, 2006 during the prosecution of the International Application No. PCT/GB2005/004539.

Al Sibae et al., "Current Trends in the Treatment of Hepatic Encephalopathy", Ther Clin Risk Manag. Jun. 2009, 5(3): 617-626.

Bosoi et al., Long term oral treatment of ornithine phenylacetate increases lean mass and attenuates brain edema in bile-duct ligated rats. Hepatology Oct. 2015, 62(Suppl 1):953A; Abstract 1523.

Bosoi et al., "Minimal Hepatic Encephalopathy Renders the Brain Susceptible to Hypotension-Induced Neuronal Cell Loss in BDL Rats", A19 from The 12th Annual Canadian Association for Study of the Liver Meeting, Feb. 2016; CA J Gastroenter Hepatol. (Feb. 2016) p. 14.

Butterworth, "Neuronal cell death in hepatic encephalopathy", Metab Brain Dis. Dec. 2007, 22(3-4): 309-320.

Ciećko-Michalska et al., "Pathogenesis of Hepatic Encephalopathy", Gastroenter Res Practice 2012, 2012: 7 pages.

Clément et al., "Bile-ligated rats are susceptible to hypotension-induced neuronal cell loss: Implications for persisting neurological complications following liver transplantation", Posters P0012; J Hepatol. Apr. 2015, 62(Suppl. 2): S295.

Dewhirst et al., "Phylogeny of the defined murine microbiota: Altered Schaedler Flora", Appl. Environ Microbiol. 1999, 65(8): 3287-3292.

Hopkins Medicine (http://www.hopkinsmedicine.org/gastroenterology_hepatology/_pdfs/liver/portal_hypertension.pdf; accessed Jun. 22, 2016); 13 pages.

Imperial College London, Clinical Trial NCT01847651; "Brain Muscle Axis during Treatment of Hepatic Encephalopathy with L-ornithine L-aspartate", May 2013, https://clinicaltrials.gov/ct2/show/NCT01847651 retrieved Oct. 16, 2016; 4 pages.

Lee et al., "Phase 2 Comparison of a Novel Ammonia Scavenging Agent with Sodium Phenylbutyrate in Patients with Urea Cycle Disorders: Safety, Pharmacokinetics and Ammonia Control", Mol Genet Metab. Mar. 2010, 100(3): 221-228.

Lucero et al., "The Role of Sarcopenia and Frailty in Hepatic Encephalopathy Management", Clin Liver Dis. Aug. 2015, 19(3): 507-528.

(56) References Cited

OTHER PUBLICATIONS

Lukkarinen, M. et al., Effect of Lysine Infusion on Urea Cycle in Lysinuric Protein Intolerance, Metabolism, May 2000, 49(5): 621-625.

Mederacke et al., "High-yield and high-purity isolation of hepatic stellate cells from normal and fibrotic mouse livers", Nat Protoc. Feb. 2015, 10(2): 305-315.

Mohamed et al., "Effect of toll-like receptor 7 and 9 targeted therapy to prevent the development of hepatocellular carcinoma", Liver Int. Mar. 2015, 35(3): 1063-1076.

Mohammad R.A. et al., Combination therapy for the treatment and prevention of hepatic encephalopathy; Ann Pharmacother. (Nov. 2012) 46(11): 1559-1563.

Mokhtarani, M. et al., "Urinary Phenylacetylglutamine as Dosing Biomarker for Patients with Urea Cycle Disorders", Mol Genet Metab. (Nov. 2012) 107(3): 308-314.

Mookerjee et al., "Increased gene and protein expression of the novel eNOS regulatory protein Nostrin and a variant in alcoholic hepatitis", Gastroenterology Jun. 2007, 132(7): 2533-2541.

Nema et al., "Excipients and Their Role in Approved Injectable Products: Current Usage and Future Directions", PDA J Pharm Sci Technol. 2011, 65(3): 287-332.

Powell et al., "Compendium of Excipients for Parenteral Formulations", PDA J Pharm Sci Technol. 1998, 52(5): 238-311.

Qiu et al., "Hyperammonemia-mediated autophagy in skeletal muscle contributes to sarcopenia of cirrhosis", Am J Physiol Endocrinal Metab. Aug. 2012, 303: E983-993.

Qiu et al., "Hyperammonemia in cirrhosis induces transcriptional regulation of myostatin by an NF-kappaB-mediated mechanism", PNAS Nov. 2013, 110(45): 18162-18167.

Rockey et al., "Randomized, Double-Blind, Controlled Study of Glycerol Phenylbutyrate in Hepatic Encephalopathy," Hepatology (2014) 59(3): 1073-1083.

Rombouts et al., "Determination and Characterization of Tetraspanin-associated Phosphoinositide-4 Kinases in Primary and Neoplastic Liver Cells", In *Lipid Signaling Protocols*, 2nd Ed. [Waugh M.G.] 2015; Chapter 17, pp. 203-212.

Romero-Gómez et al., "Hepatic encephalopathy in patients with acute decompensation of cirrhosis and acute-on-chronic liver failure", J Hepatol. Feb. 2015, 62(2): 437-447.

Shen et al., "Engineering the gut microbiota to treat hyperammonemia", J Clin Invest. Jun. 2015, 125(7): 2841-2850.

Thomsen et al., "Experimental nonalcoholic steatohepatitis compromises ureagenesis, an essential hepatic metabolic function", Am J Physiol Gastrointest Liver Physiol. Jun. 2014, 307(3): G295-301.

Torres-Vega et al., "Delivery of Glutamine Synthetase Gene by Baculovirus Vectors: A Proof of Concept for the Treatment of Acute Hyperammonemia", Gene Ther., Jan. 2015, 33(1): 58-64.

Ventura-Cots et al., Safety of ornithine phenylacetate in cirrhotic decompensated patients: an open-label, dose-escalating, single-cohort study; J Clin Gastroenter. (2013) 47(10): 881-887.

Walrand S., "Ornithine alpha-ketoglutarate: Could it be a new therapeutic option for sarcopenia?" J Nutr Health Aging. Aug. 2010, 14(7): 570-577.

Zhu Q. et al., Rifaximin Attenuates Bile Duct Ligation Induced Liver Fibrosis and Portal Hypertension Through Inhibition of the TLR4 Pathway; Gastroenterology (May 2011) 140(5) Suppl 1: S903; Abstract 732.

Zhu Q. et al., Intestinal decontamination inhibits TLR4 dependent fibronectin mediated crosstalk between stellate cells and endothelial cells in liver fibrosis in mice; J Hepatol. (Apr. 2012) 56(4): 893-899.

Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.

Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.

Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.

Office Action dated Jul. 26, 2017 for Indian Application No. 50/CHENP/2012, filed Jun. 8, 2010.

Office Action dated Mar. 14, 2017 for Canadian Application No. 2764587, filed Jun. 8, 2010.

Office Action dated Jan. 6, 2015 for Chinese Application No. 2011103045617, filed Nov. 28, 2005.

Office Action dated Mar. 20, 2017 for Chinese Application No. 201410350083.7, filed Jul. 22, 2014.

Office Action dated May 24, 2016 for Eurasian Application No. 201500650 filed Jul. 16, 2015.

Extended Search Report dated Oct. 31, 2012 for European Application No. 10786721.0, filed Jun. 9, 2010.

Office Action dated Feb. 23, 2017 for Japanese Application No. 2015-098205, filed May 13, 2015.

Office Action dated Sep. 5, 2017 for Japanese Application No. 2015-098205, filed May 13, 2015.

Decision to Grant Patent dated Nov. 11, 2017 for Japanese Application No. 2015-098205, filed May 13, 2015.

Office Action dated May 23, 2017 for Korean Application No. 10-2017-7005930, filed Mar. 2, 2017.

Ocera Therapeutics, Inc., News Release: Ocera Initiates Phase 1 Clinical Trial of Oral Drug Candidate OCR-002 for Prevention of Hepatic Encephalopathy; Globe Newswire; Sep. 16, 2015, 4 pages.

Oria et al., "Ornithine phenylacetate prevents disturbances of motor-evoked potentials induced by intestinal blood in rats with portacaval anastomosis", J Hepatol. Jan. 2012, 56(1): 109-114.

Puche et al., "Hepatic stellate cells and liver fibrosis", Comprehensive Physiol. 2013, 3:1473-1491.

Australian Examination Report dated Sep. 3, 2015 for Application No. 201450643, filed Oct. 15, 2014.

Australian Office Action dated Jul. 1, 2016 for Application No. 201450643, filed Oct. 15, 2014.

Eurasian Office Action dated Jun. 18, 2018 for Application No. 201691430 filed Aug. 12, 2016.

Israel Office Action dated Feb. 1, 2017 for Application No. 248696, filed Nov. 2, 2016.

Israel Office Action dated Nov. 19, 2018 for Application No. 248696, filed Nov. 2, 2016.

Japanese Office Action dated Jun. 26, 2018 for Application No. 2016-238546, filed Dec. 8, 2016.

Korean Office Action dated May 23, 2017 for Application No. 10-2017-7005930, filed Mar. 2, 2017.

Bosoi et al., "Oral Ornithine Phenylacetate Attenuates Muscle Mass Loss and Prevents Hepatic Encephalopathy in BDL Rats", Abstract 23; J Clin Exper Hepatol. (Feb. 2017) 7:S18-S19.

Canbay et al. "L-Ornithine L-Aspartate (LOLA) as a Novel Approach for Therapy of Non-alcoholic Fatty Liver Disease", Drugs 2019, vol. 79(Suppl 1), pp. S39-S44 (first published online Jan. 31, 2019).

Clément et al., "Minimal hepatic encephalopathy leads to hypotension-induced neuronal cell loss in BDL rats", Abstract 51; Hepatology (Oct. 2015) 62(Suppl 1):233A-234A.

Efrati et al., "Effect of sodium benzoate on blood ammonia response to oral glutamine challenge in cirrhotic patients: a note of caution", Am J Gastroenterol. (2000) 95(12):3574-3578. (Abstract).

Feuerstein et al., Cytokines, Inflammation, and Brain Injury: Role of Tumor Necrosis Factor-α. Cerebrovasc Brain Metab Rev. 1994, 6(4):341-360.

Islam et al., "Sorbitol and lactitol reduce body fat and toxic ammonia levels in rats", Nutrition Res. (2007) 27:440-447.

Maruzen Co., Ltd., "Jikken Kagaku Guide Book (Experimental Chemistry Guide Book)," The Chemical Society of Japan, 1992, 3rd Edition, pp. 130-131.

Maruzen Co., Ltd., "Jikken Kagaku Koza (Zoku) Experimental Chemistry Course (cont.)", 2. Bunri to Seisei (Isolation and Purification), Jan. 25, 1967, pp. 159-162 and 184-193.

Pahan et al., Lovastatin and Phenylacetate Inhibit the Induction of Nitric Oxide Synthase and Cytokines in Rat primary Astrocytes, Microglia, and Macrophages, J Clin Invest. BMJ Group GB, 1997, 100(11):2671-2679.

(56) References Cited

OTHER PUBLICATIONS

Roque et al., "32* Pro-inflammatory effects of sodium 4-phenylbutyrate in CF lung epithelial cells containing F508del-CFTR", J Cystic Fibrosis 2007, 6: S7.
Smirnov et al., "Ammonia Neutralization and Urea Synthesis in Cardiac Muscle", Circ Res. 1974, 35(Suppl 3):58-73.
Vilatoba et al., Sodium 4-phenylbutyrate protects against liver ischemia reperfusion injury; Surgery, 2005, 138(2):342-351.
Yoneda et al., "Treatment for non-alcoholic steatohepatitis", Separate Igakuno Ayumi, Digestive diseases—state of arts Ver. 3, Oct. 10, 2006, pp. 370-372.
Brazilian Office Action dated Oct. 17, 2018 for Application No. PI1012956-1, filed Jun. 8, 2010.
Canadian Office Action dated Mar. 8, 2019 for Application No. 2997484, filed Mar. 5, 2018.
Eurasian Search Report dated Jun. 18, 2019 in Application No. 201691430 filed Aug. 12, 2016.
European Extended Search Report dated Jun. 27, 2019 for Application No. 19158338.4, filed Feb. 20, 2019.
Hanouneh et al. "Rifaximin prevents spontaneous bacterial peritonitis and improves transplant free survival in patients with liver cirrhosis." Gastroenterology (2011) 140(5): S-903.
Toshikuni et al., "Nutrition and exercise in the management of liver cirrhosis", World J Gastroenterol. (Jun. 2014), 20(23):7286-7297.
Wan et al., "L-ornithine phenylacetate, a new medicine to treat hepatic encephalopathy", Chinese J New Drugs, 2013, 22(11):1274-1277.

FIGURE 1A-D
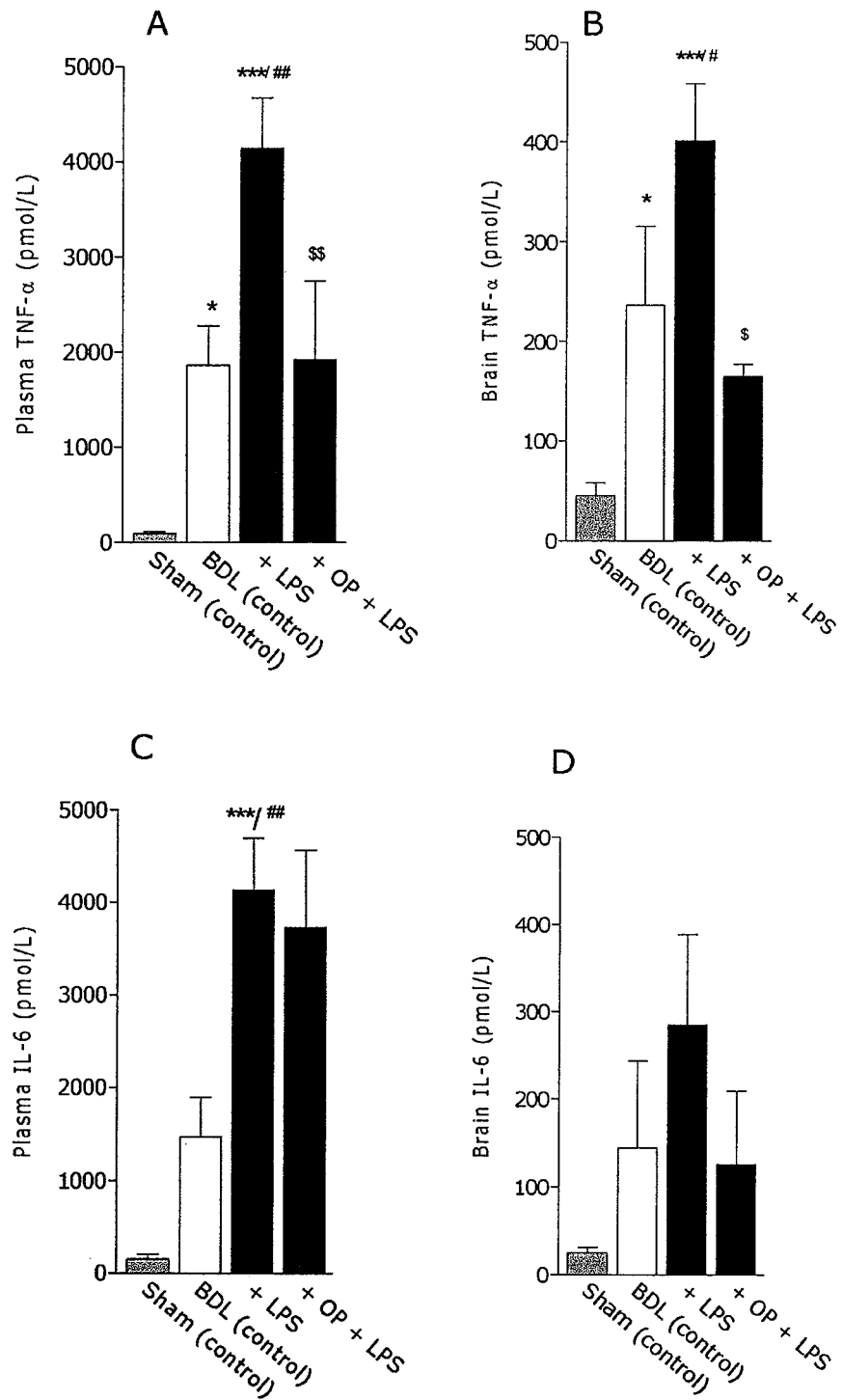

FIGURE 2A-B
A. Brain iNOS expression
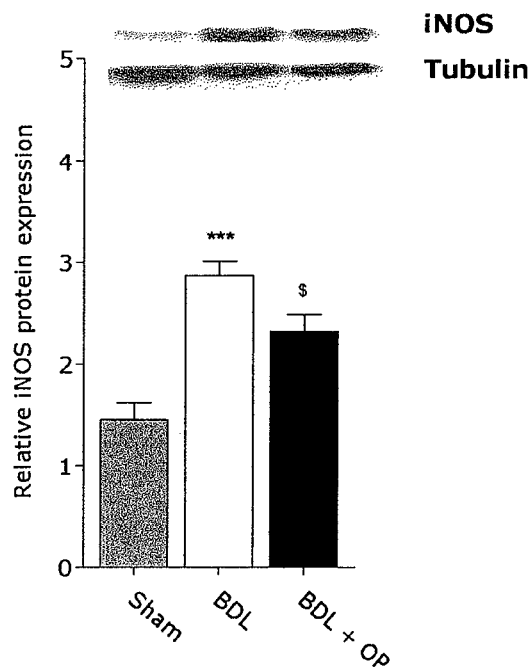
B) Brain NFκB expression
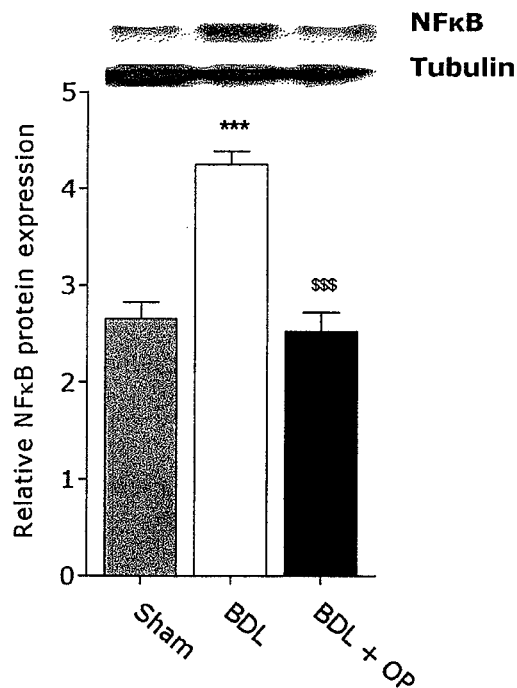

FIGURE 3A-B
A.
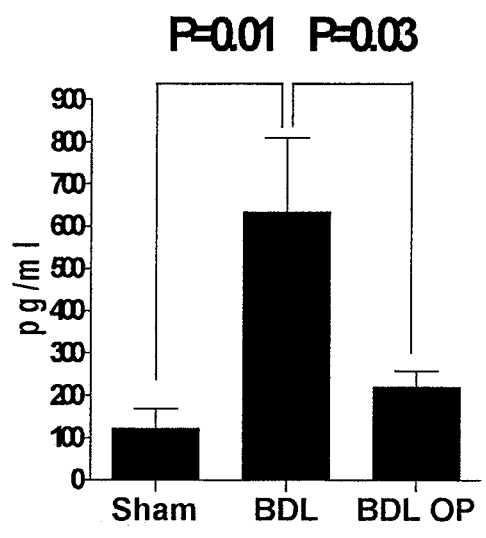
B.
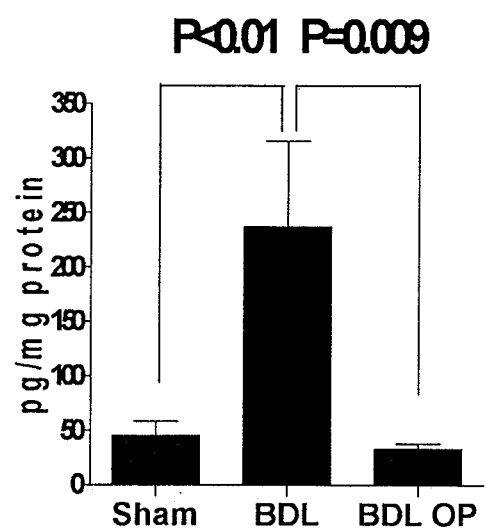

FIGURE 4A-C
A.
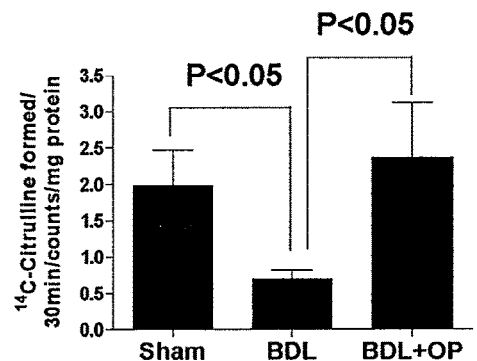
B.
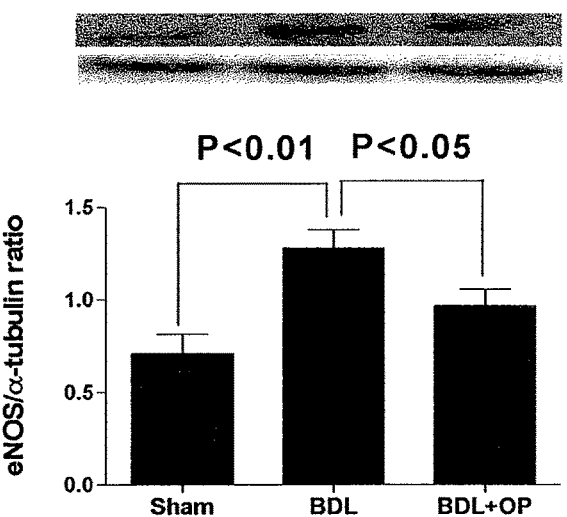
C.
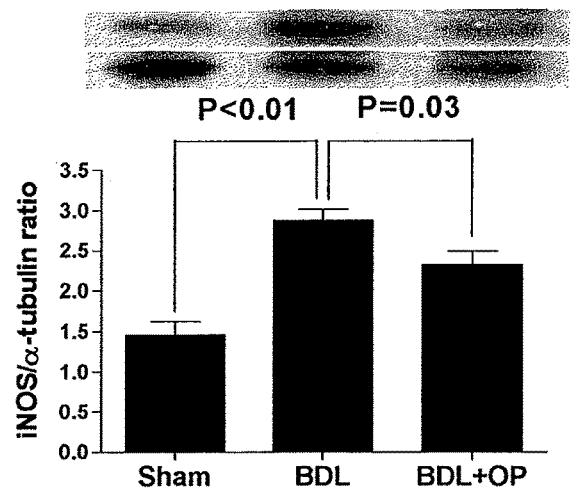

FIGURE 5A-C
A.
B.
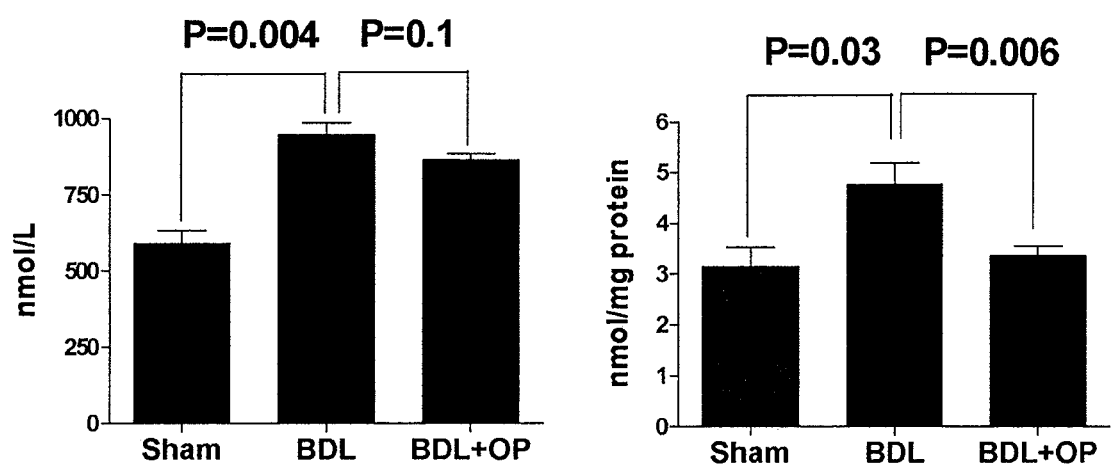
C.
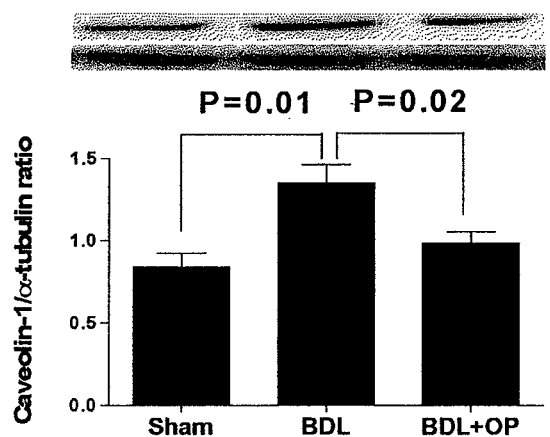

FIGURE 6A-C
A.
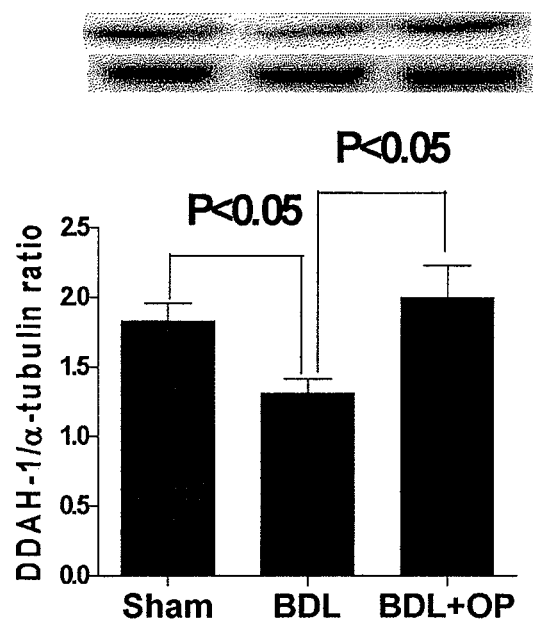
B.
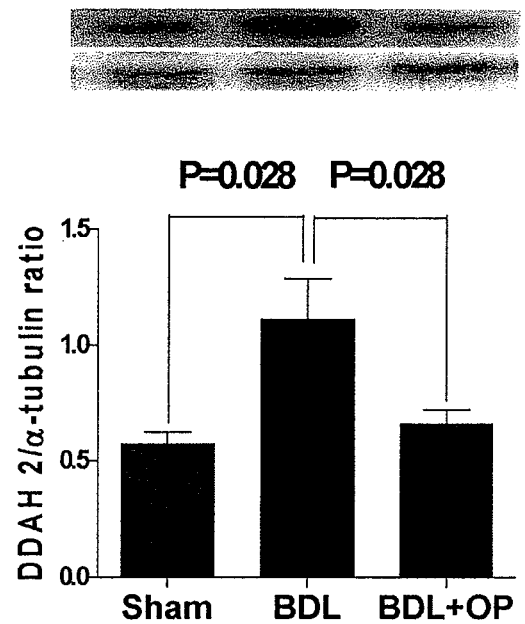
C.
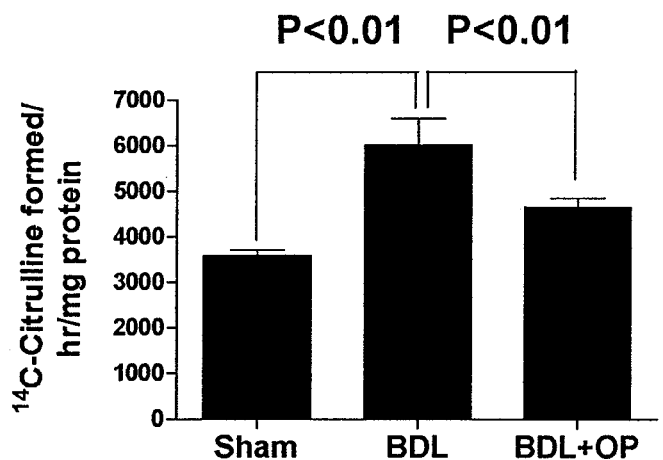

FIGURE 7A-C
A. Hepatic eNOS activity
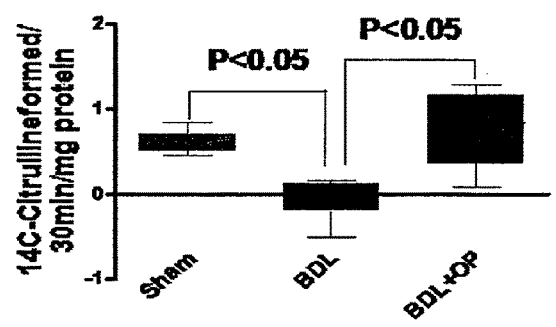
B. Hepatic eNOS protein expression
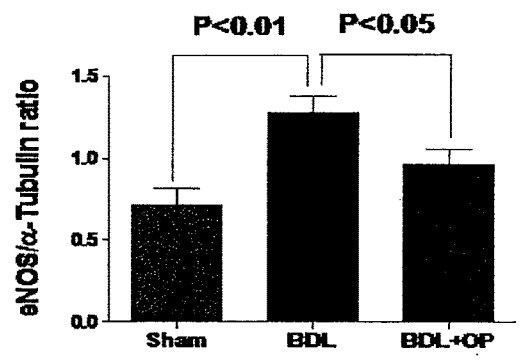
C. Hepatic DDAH-1 protein expression
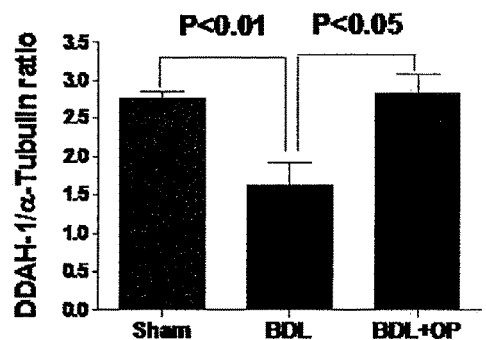

FIGURE 7D-F
D. Hepatic NFkB protein expression
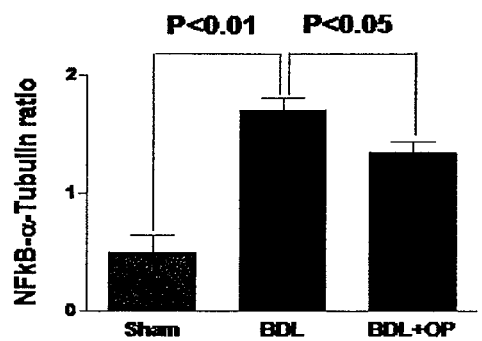
E. Hepatic caveolin-1 protein expression
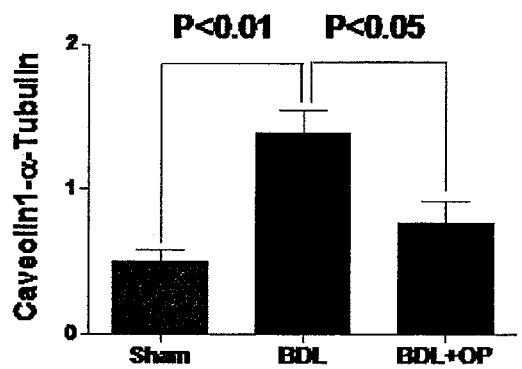
F. Portal pressure
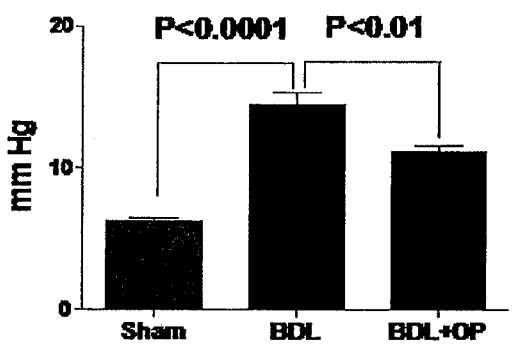

TREATMENT OF PORTAL HYPERTENSION AND RESTORATION OF LIVER FUNCTION USING L-ORNITHINE PHENYLACETATE

CROSS-REFERENCE TO RELATED APPLICATIONS

This application is a continuation application of U.S. patent application Ser. No. 13/375,463, filed on Feb. 17, 2012, which is a U.S. National Phase under 35 U.S.C. § 371 of International Application No. PCT/US2010/037838, entitled TREATMENT OF PORTAL HYPERTENSION AND RESTORATION OF LIVER FUNCTION USING L-ORNITHINE PHENYLACETATE, filed on Jun. 8, 2010, and published on Dec. 16, 2010 as WO 2010/144498, which claims the benefits of U.S. Provisional Patent Application No. 61/185,158 filed Jun. 8, 2009, U.S. Provisional Patent Application No. 61/240,748 filed Sep. 9, 2009 and U.S. Provisional Patent Application No. 61/296,377 filed Jan. 19, 2010. The contents of each of these related applications are hereby incorporated by reference in their entirety.

BACKGROUND

Field

The present application relates to the fields of pharmaceutical chemistry, biochemistry and medicine. One aspect relates to the treatment and/or prevention of portal hypertension using L-ornithine in combination with at least one of phenylacetate and phenylbutyrate. Another aspect relates to restoration of liver function using L-ornithine in combination with at least one of phenylacetate and phenylbutyrate.

Description of the Related Art

Portal hypertension is an increase in the blood pressure within the portal vein and its tributaries. It is a condition that can develop in patients with liver disease such as cirrhosis and hepatic fibrosis. Portal hypertension may also be caused by scarring of the liver, thrombosis, or clotting in the portal vein.

Various prevention, treatment and management strategies for portal hypertension are currently available depending upon the severity of the symptoms. There is a need for additional therapies for treat the above conditions.

SUMMARY

Some embodiments disclose methods of treating portal hypertension in a subject, comprising administering to the subject L-ornithine in combination with at least one of phenylacetate and phenylbutyrate, thereby reducing portal hypertension.

Some embodiments disclose methods of delaying or reducing the likelihood of onset of portal hypertension in a subject, comprising administering to the subject L-ornithine in combination with at least one of phenylacetate and phenylbutyrate, thereby delaying the onset of portal hypertension.

Some embodiments disclose methods of restoring liver function in a subject having poor liver function, comprising administering to the subject L-ornithine in combination with at least one of phenylacetate and phenylbutyrate, thereby improving liver function.

Some embodiments disclose methods of treating variceal bleeding in a subject suffering from portal hypertension, comprising administering to the subject L-ornithine in combination with at least one of phenylacetate and phenylbutyrate, thereby reducing the variceal bleeding.

Some embodiments disclose methods of treating ascites in a subject suffering from portal hypertension, comprising administering to the subject L-ornithine in combination with at least one of phenylacetate and phenylbutyrate, thereby reducing ascites.

Some embodiments disclose methods of protecting against brain injury in a patient with acute liver failure, the method comprising identifying a patient as suffering from acute liver failure and administering to the patient L-ornithine in combination with at least one of phenylacetate and phenylbutyrate, thereby reducing the likelihood that the patient will develop brain injury. In some embodiments, the administering occurs immediately after said identifying. Some embodiments further comprise treating the acute liver failure. In some embodiments, the treating comprises liver transplantation. Some embodiments further comprise treating a complication caused by the acute liver failure. In some embodiments, the complication comprises variceal bleeding.

In some embodiments, the subject is suffering from portal hypertension. In some embodiments, the subject with portal hypertension also suffers from liver disease, such as cirrhosis. In some embodiments, the subject is suffering from liver disease. In some embodiments, the subject with liver disease also suffers from portal hypertension. In some embodiments, the liver disease is a chronic liver disease (for example, cirrhosis) or an acute liver failure. In some embodiments, the treatment of portal hypertension is achieved by reducing the level of proinflammatory cytokines in the subject. In some embodiments, the treatment of portal hypertension is achieved by increasing endothelial nitric oxide synthase activity. In some embodiments, L-ornithine and phenylacetate is administered as L-orthine phenyl acetate. In some embodiments, separate physiologically acceptable salts of L-ornithine and at least one of phenylacetate and phenylbutyrate are administered to the subject. In some embodiments, L-ornithine is present administered as a free monomeric amino acid or physiologically acceptable salt thereof. In some embodiments, at least one of phenylacetate and phenylbutyrate is administered as a sodium phenylacetate or sodium phenylbutyrate. In some embodiments, administration is oral, intravenous, intraperitoneal, intragastric, or intravascular administration. In some embodiments, improving liver function reduces the portal hypertension. In some embodiments, improving liver function comprises increasing liver perfusion. In some embodiments, the dose of the L-ornithine and the phenylacetate or phenylbutyrate administered is between 20 g and 40 g.

BRIEF DESCRIPTION OF THE DRAWINGS

FIG. 1A-D. Plasma and TNF-α expression: Shows that compared with sham-operated controls, there was A) a significant increase in plasma TNF-α in bile duct ligation (BDL) rats (*$p<0.05$), which was markedly augmented by administration of lipopolysaccharide (LPS) (##$p<0.01$), and ameliorated by administration of L-ornithine, phenylacetate (OP) treatment; B) a significant increase in brain TNF-α in BDL rats (*$p<0.05$), which was markedly augmented by administration of LPS (#$p<0.05$), and ameliorated by administration of OP treatment ($$p<0.05$); C) a near significant increase in plasma IL-6 in BDL rats was augmented by administration of LPS (##$p<0.01$); and D) although there were similar trends in IL-6 brain concentrations with BDL and treatment intervention by OP failed to reach significance.

FIG. 2A-B. Brain iNOS and NFkB expression: Shows that compared with sham-operated controls, there was A) a significant increase in brain iNOS protein expression in BDL rats (*p<0.01), which was ameliorated by administration of OP ($p<0.01); and B) a significant increase in NFkB in BDL rats (*p<0.05), which was also ameliorated by administration of OP ($$$p<0.01). These were associated with significant reduction in arterial and brain TNFa, IL1b and IL-6 in the OP treated animals.

FIG. 3A-B. Plasma and brain TNF-α levels: Shows that compared to sham controls, there was A) a significant elevation in plasma TNF-α level in BDL rats, which was reversed by administration of OP; and B) a significant elevation in plasma TNF-α level in BDL rats, which was also reversed by administration of OP.

FIG. 4A-C. eNOS activity and protein expression, and iNOS protein expression: Shows that compared to sham controls, there was A) a significant decrease in eNOS activity in BDL rats, which was reversed by administration of OP; B) an increase in eNOS protein expression in BDL rats; and C) a significant increase in iNOS protein expression in BDL rats.

FIG. 5A-C. Plasma ADMA and cerebral caveolin-1 protein expression: Shows that compared to sham control, there was A) a significant increase in plasma ADMA in BDL rat plasma, which was non-significantly reduced after administration of OP; B) a significant increase in plasma ADMA in BDL brain homogenates, which was significantly reduced by administration of OP; and C) a significant increase in cerebral caveolin-1 protein expression in BDL rat, which was reversed by administration of OP.

FIG. 6A-C. Cerebral DDAH-1 and DDAH-2 protein expression and activity: Shows that compared to sham control, there was A) a significant decrease in cerebral DDAH-1 protein expression in BDL rats, which was reversed by administration of OP; B) a significant increase in cerebral DDAH-2 protein expression in BDL rats, which was reversed by administration of OP; and C) a significant increase in DDAH activity in BDL rat brain, which was reversed by administration of OP.

FIG. 7A-F. eNOS activity and protein expression, protein expression of DDAH-1, NFκ-B, hepatic caveolin-1, and portal pressure: Show that compared to sham control, there was A) a significant decrease in eNOS activity in BDL rats, which was reversed by administration of OP; B) a significant increase in eNOS protein expression in BDL rats, which was also reversed by administration of OP; C) a significant increase in DDAH-1 protein expression in BDL rats, which was reversed by administration of OP; D) a significant increase in NFκ-B protein expression in BDL rats and the increase was significantly reduced by administration of OP; E) a significant increase in caveolin-1 protein expression in BDL rats and the increase was significantly reduced by administration of OP; and F) a significant increase in portal pressure in BDL rats and the administration of OP resulted in a 30% reduction of portal pressure.

DETAILED DESCRIPTION

Definitions

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "administration" or "administering" refers to a method of giving a dosage of a pharmaceutically active ingredient to a vertebrate.

As used herein, a "dosage" refers to an amount of therapeutic agent administered to a patient.

As used herein, a "daily dosage" refers to the total amount of therapeutic agent administered to a patient in a day.

As used herein, the term "therapeutic agent" means a substance that is effective in the treatment of a disease or condition.

As used herein, "therapeutically effective amount" or "pharmaceutically effective amount" is meant an amount of therapeutic agent, which has a therapeutic effect. The dosages of a pharmaceutically active ingredient which are useful in treatment are therapeutically effective amounts. Thus, as used herein, a therapeutically effective amount means those amounts of therapeutic agent which produce the desired therapeutic effect as judged by clinical trial results and/or model animal studies.

As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

Abbreviations

BDL=bile duct ligation;
OP=ornithine, phenylacetate;
LPS=lipopolysaccharide.
iNOS=inducible nitric oxide synthase
eNOS=endothelial nitric oxide synthase Portal Hypertension Portal hypertension is an increase in the pressure within the portal vein (the vein that carries the blood from the digestive organs to the liver). The main symptoms and complications of portal hypertension include, but are not limited to, gastrointestinal bleeding, for example, black, tarry stools or blood in the stools, or vomiting of blood due to the spontaneous rupture and hemorrhage from varices; ascites, for example, an accumulation of fluid in the abdomen; encephalopathy, for example, confusion and forgetfulness caused by poor liver function and the diversion of blood flow away from the liver; and reduced levels of platelets or decreased white blood cell count.

Portal hypertension can be a symptom or a result of an underlying condition (e.g., liver disorder), and therefore a subject may have portal hypertension that is associated with a one or more conditions. In some embodiments, the portal hypertension is associated with a liver disease.

Non-limiting examples of liver disease include intrahepatic cholestasis (alagille syndrome, biliary liver cirrhosis), fatty liver (alcoholic fatty liver, reye syndrome), hepatic vein thrombosis, hepatolentricular degeneration, hepatomegaly, liver abscess (amebic liver abscess), liver cirrhosis (alcoholic, biliary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome). In some embodiments, the liver disorder is hepatitis, cirrhosis, cholestasis or liver failure. In some embodiments, a subject suffering from a liver disease has hepatic encephalopathy.

In some embodiments, the portal hypertension is associated with a chronic liver disease. In some embodiments, the chronic liver disease is cirrhosis. In cirrhosis, the scar tissue blocks the flow of blood through the liver, which consequently results in portal hypertension. Increased pressure in the portal vein causes large veins (varices) to develop across the esophagus and stomach to bypass the blockage. The pressure in the varices increases and may rupture. In some embodiments, reducing portal hypertension reduces the likelihood of onset of hepatic encephalopathy.

Portal hypertension may also be caused by thrombosis or clotting in the portal vein. Portal hypertension in humans and laboratory animals can be associated with a hyperkinetic circulation, vasodilation in the splanchnic territory and a hypersplenism. The hypersplenism can lead to an important pancytopenia.

Treatment of Portal Hypertension

In some embodiments, L-ornithine is co-administered with phenylacetate or phenylbutyrate to a subject to treat and/or prevent portal hypertension. In some embodiments, L-ornithine is co-administered with phenylacetate or phenylbutyrate to a subject to delay or reduce the likelihood of the onset of portal hypertension. In some embodiments, the treatment results in restoration of liver function (e.g., increasing liver perfusion) and thereby improves portal hypertension. In some embodiments, partial liver function is restored. In some embodiments, entire liver function is restored. Restoration of liver function (e.g., increasing liver perfusion) may be indicated by one or more of the following measurements: the alanine transaminase (ALT) test, aspartate aminotransferase (AST) test, alpha glutathione S-transferase (GST) test, albumin (Alb) test, prothrombin time test, and composite scores (for example, child-pugh score' MELD score). Additionally, liver hemodynamics can be measured by detecting liver blood flow and/or portal pressure.

In some embodiments, the co-administration of L-ornithine and phenylacetate or phenylbutyrate results in modulating of endothelial nitric oxide synthase (eNOS) activity, and thereby treat or ameliorate one or more symptoms associated with decreased eNOS activity. In some embodiments, the decreased eNOS activity is associated with an increase in endogenous nitric oxide synthase inhibitors, including Caveolin-1 and asymmetric-dimethylarginine (ADMA). In some embodiments, the decreased eNOS activity is associated with an increase in NFκB. In some embodiments, the decreased eNOS activity is associated with an increase in ammonia. In some embodiments, the decreased eNOS activity is associated with a liver disease, including chronic liver disease (for example, cirrhosis) and acute liver failure. In some embodiments, the co-administration is used to treat hepatic inflammation. In some embodiments, the co-administration is used to improve the function of organ systems that have deranged nitric oxide signaling in liver disease (for example, cirrhosis).

In some embodiments, the co-administration is useful to reduce pro-inflammatory cytokines, which further promotes its ability to treat or reduce the likelihood of portal hypertension. In some embodiments, portal hypertension is prevented in patients with existing chronic liver disease such as cirrhosis by the administration of the combination. Thus, in some embodiments, the combination is administered to a patient having chronic liver disease also having a portal hypertension. In some embodiments, the co-administration is used to restore partial or entire liver function.

While not being bound by any particular theory, in some embodiments, the co-administration prevents or relieves the condition of portal hypertension through effects on inflammatory pathways. In some embodiments, decreasing the level of inflammatory cytokines and/or iNOS (inducible nitric oxide synthase) results in the restoration of partial or complete liver function and treatment of portal hypertension.

The L-ornithine and phenylacetate or phenylbutyrate may be administered separately or in a single dosage form. In one embodiment, the combination is administered as the L-ornithine phenylacetate salt or as a solution of the L-ornithine phenylacetate salt.

Different forms of composition of L-ornithine in combination with at least one of phenylacetate (or phenyl acetate salts) and phenylbutyrate are described in U.S. Patent Publication No. US2008/0119554 and U.S. patent application Ser. No. 12/753,763 filed Apr. 2, 2010, which are hereby incorporated by reference in their entireties. In some embodiments, L-ornithine and phenylacetate is present and/or administered as L-orthine phenyl acetate or physiologically acceptable salt thereof. In some embodiments, L-ornithine is present and/or administered as a free monomeric amino acid or physiologically acceptable salt thereof. In some embodiments, at least one of phenylacetate and phenylbutyrate is present and/or administered as a sodium phenylacetate or sodium phenylbutyrate. In some embodiments, a physiologically acceptable salt of L-ornithine and a physiologically acceptable salt of at least one of phenylacetate and phenylbutyrate are administered to the subject.

Protection Against Brain Injury

In other embodiments, L-ornithine is co-administered with phenylacetate or phenylbutyrate to a subject with acute liver failure or acute liver decompensation in subjects with chronic liver disease to protect against brain injury. In some embodiments, the combination is administered prophylactically to a subject at risk of acute liver failure (e.g., a subject with a Tylenol overdose who has not yet manifested acute liver failure) or having chronic liver disease without acute liver decompensation. While not being bound by any particular theory, in some embodiments, early administration of L-ornithine with phenylacetate or phenylbutyrate to a patient with acute liver failure or acute liver decompensation can prevent brain injury from developing through its action on suppressing inflammatory pathways as described herein. Accordingly, in some embodiments, L-ornithine is co-administered with phenylacetate or phenylbutyrate prior to or immediately upon diagnoses with acute liver failure or acute liver decompensation, regardless of the further course of treatment, which may include liver transplantation. In some embodiments, such early administration prevents variceal bleeding, onset of encephalopathy, onset of raised intracranial pressure, onset of coma, need for intubation and ICU treatment, and mitigates or reverses hyperammonemia, and thereby protects against brain injury caused by such complications.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The ornithine and the phenylacetate and/or phenylbutyrate can be formulated for administration with a pharmaceutically acceptable carrier or diluent. The ornithine and the phenylacetate and/or phenylbutyrate can be formulated as a medicament with a standard pharmaceutically acceptable carrier(s) and/or excipient(s) as is routine in the pharmaceutical art. The exact nature of the formulation will depend upon several factors including the desired route of administration. Typically, ornithine and the phenylacetate and/or phenylbutyrate are formulated for oral, intravenous, intragastric, intravascular or intraperitoneal administration.

The term "pharmaceutical composition" refers to a mixture of a compound or compounds disclosed herein with other chemical components, such as diluents or carriers. The pharmaceutical composition facilitates administration of the compound(s) to an organism. Multiple techniques of administering a compound exist in the art including, but not limited to, oral, injection, aerosol, parenteral, and topical administration. Pharmaceutical compositions can also be obtained by reacting compound(s) with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines a chemical compound diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compound or combination of compounds disclosed herein may be found in "Remington's Pharmaceutical Sciences," Mack Publishing Co., Easton, Pa., 18th edition, 1990.

Some embodiments provide the compound(s) or combination of compounds disclosed herein in tablets, film coated tablets, capsules, caplets, pills, gel caps, pellets, beads, or dragee dosage forms. Preferably, the formulations disclosed herein can provide favorable drug processing qualities, including, for example, but not limited to, rapid tablet press speeds, reduced compression force, reduced ejection forces, blend uniformity, content uniformity, uniform dispersal of color, accelerated disintegration time, rapid dissolution, low friability (preferable for downstream processing such as packaging, shipping, pick-and-pack, etc.) and dosage form physical characteristics (e.g., weight, hardness, thickness, friability) with little variation.

The compound(s) or combination of compounds disclosed herein can be formulated readily, for example, by combining the drug substance with any suitable pharmaceutically acceptable excipient(s) for example, but not limited to, binders, diluents, disintegrants, lubricants, fillers, carriers, coatings, glidants, flavours, color additives, and the like, as set forth below. Such compositions can be prepared for storage and for subsequent processing.

Excipients

Acceptable excipients for therapeutic use are well known in the pharmaceutical art, and are described, for example, in Handbook of Pharmaceutical Excipients, 5th edition (Raymond C Rowe, Paul J Sheskey and Sian C Owen, eds. 2005), and Remington: The Science and Practice of Pharmacy, 21st edition (Lippincott Williams & Wilkins, 2005), each of which is hereby incorporated in its entirety. The term "carrier" material or "excipient" herein can mean any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule, tablet, film coated tablet, caplet, gel cap, pill, pellet, bead, and the like suitable for oral administration. Excipients can include, by way of illustration and not limitation, diluents, disintegrants, binding agents, wetting agents, polymers, lubricants, glidants, coatings, sweetens, solubilizing agents substances added to mask or counteract a disagreeable taste or odor, flavors, colorants, fragrances, and substances added to improve appearance of the composition.

The compositions and formulations can include any other agents that provide improved transfer, delivery, tolerance, and the like. These compositions and formulations can include, for example, powders, pastes, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax.

Any of the foregoing mixtures can be appropriate in treatments and therapies in accordance with the disclosure herein, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32(2):210-8 (2000), Charman W N "Lipids, lipophilic drugs, and oral drug delivery-some emerging concepts." J. Pharm. Sci. 89(8):967-78 (2000), and the citations therein for additional information related to formulations, excipients and carriers well known to pharmaceutical chemists.

In some embodiments, one or more, or any combination of the listed excipients can be specifically included or excluded from the formulations and/or methods disclosed herein. As will be appreciated by those of skill in the art, the amounts of excipients will be determined by drug dosage and dosage form size.

Lubricants

In some embodiments, lubricants are employed in the manufacture of certain dosage forms. For example, a lubricant will often be employed when producing tablets. In some embodiments, a lubricant can be added just before the tableting step, and can be mixed with the formulation for a minimum period of time to obtain good dispersal. In some embodiments, one or more lubricants can be used. Examples of suitable lubricants include, but are not limited to, magnesium stearate, calcium stearate, zinc stearate, stearic acid, talc, glyceryl behenate, polyethylene glycol, polyethylene oxide polymers (for example, available under the registered trademarks of Carbowax® for polyethylene glycol and Polyox® for polyethylene oxide from Dow Chemical Company, Midland, Mich.), sodium lauryl sulfate, magnesium lauryl sulfate, sodium oleate, sodium stearyl fumarate, DL-leucine, colloidal silica, and others as known in the art. Typical lubricants are magnesium stearate, calcium stearate, zinc stearate and mixtures of magnesium stearate with sodium lauryl sulfate.

Color Additives

In some embodiments, color additives also can be included. The colorants can be used in amounts sufficient to distinguish dosage form strengths. Preferably, color additives approved for use in drugs (21 CFR 74, which is incorporated herein by reference in its entirety) are added to the commercial formulations to differentiate tablet strengths. The use of other pharmaceutically acceptable colorants and combinations thereof are encompassed by the current disclosure.

Binders

Binders can be used, for example, to impart cohesive qualities to a formulation, and thus ensure that the resulting dosage form remains intact after compaction. Suitable binder materials include, but are not limited to, microcrystalline cellulose, gelatin, sugars (including, for example, sucrose, glucose, dextrose and maltodextrin), polyethylene glycol, waxes, natural and synthetic gums, polyvinylpyrrolidone, pregelatinized starch, povidone, cellulosic polymers (including, for example, hydroxypropyl cellulose (HPC), hydroxypropyl methylcellulose (HPMC), methyl cellulose, hydroxyethyl cellulose, and the like), hydroxypropyl cellulose (HPC), and the like. Accordingly, in some embodiments, the formulations disclosed herein can include at least one binder to enhance the compressibility of the major excipient(s). In some embodiments, the binder(s) is(are) sprayed on from solution, e.g. wet granulation, to increase binding activity.

Disintegrants

In some embodiments, disintegrants are used, for example, to facilitate tablet disintegration after administration, and are generally starches, clays, celluloses, algins, gums, or crosslinked polymers. Suitable disintegrants include, but are not limited to, crosslinked polyvinylpyrrolidone (PVP-XL), sodium starch glycolate, alginic acid, methacrylic acid DYB, microcrystalline cellulose, crospovidone, polacriline potassium, sodium starch glycolate, starch, pregelatinized starch, croscarmellose sodium, and the like. If desired, the pharmaceutical formulation can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, sodium lauryl sulfate, dioctyl sodium sulfosuccinate, polyoxyethylene sorbitan fatty acid esters, etc. and the like.

Coatings

In some embodiments, the formulations can include a coating, for example, a film coating. Where film coatings are involved, coating preparations can include, for example, a film-forming polymer, a plasticizer, or the like. Also, the coatings can include pigments and/or opacifiers. Non-limiting examples of film-forming polymers include hydroxypropyl methylcellulose, hydroxypropyl cellulose, methylcellulose, polyvinyl pyrrolidine, and starches. Non-limiting examples of plasticizers include polyethylene glycol, tributyl citrate, dibutyl sebecate, castor oil, and acetylated monoglyceride. Furthermore, non-limiting examples of pigments and opacifiers include iron oxides of various colors, lake dyes of many colors, titanium dioxide, and the like.

Diluents

In some embodiments, diluents are used, and are generally selected from one or more of the compounds sucrose, fructose, glucose, galactose, lactose, maltose, invert sugar, calcium carbonate, lactose, starch, microcrystalline cellulose, lactose monohydrate, calcium hydrogen phosphate, anhydrous calcium hydrogen phosphate, a pharmaceutically acceptable polyol such as xylitol, sorbitol, maltitol, mannitol, isomalt and glycerol, polydextrose, starch, or the like, or any mixture thereof.

Surfactants

In some embodiments, surfactants are used. The use of surfactants as wetting agents in oral drug forms is described in the literature, for example in H. Sucker, P. Fuchs, P. Speiser, Pharmazeutische Technologie, 2nd edition, Thieme 1989, page 260. It is known from other papers, such as published in Advanced Drug Delivery Reviews (1997), 23, pages 163-183, that it is also possible to use surfactants, inter alia, to improve the permeation and bioavailability of pharmaceutical active compounds. Examples of surfactants include, but are not limited to, anionic surfactants, non-ionic surfactants, zwitterionic surfactants and a mixture thereof. Preferably, the surfactants is selected from the group consisting of poly(oxyethylene) sorbitan fatty acid ester, poly (oxyethylene) stearate, poly(oxyethylene) alkyl ether, polyglycolated glyceride, poly(oxyethylene) caster oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate, and the like, and a mixture thereof.

Glidants

In some embodiments, glidants are used. Examples of glidants which may be used include, but are not limited to, colloidal silicon dioxide, magnesium trisilicate, powdered cellulose, starch, talc and calcium phosphate, or the like, and mixtures thereof.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound or combination of compounds disclosed herein can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present disclosure may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present disclosure thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compound(s) or combination of compounds disclosed herein can be formulated readily by combining the active compound with pharmaceutically acceptable carriers well known in the art. Such carriers enable the compound or combination of compounds disclosed herein to be formulated as tablets, film coated tablets, pills, dragees, capsules, liquids, gels, get caps, pellets, beads, syrups, slurries, suspensions and the like, for oral ingestion by a patient to be treated. Pharmaceutical preparations for oral use can be obtained by combining the active compound with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. In addition, stabilizers can be added. All formulations for oral administration should be in dosages suitable for such administration. In some embodiments, formulations of the compound(s) or combination of compounds disclosed herein with an acceptable immediate release dissolution profile and a robust, scalable method of manufacture are disclosed.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compound or combination of compounds disclosed herein is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., Clin. Ther., 23(3):440-50 (2001)) or hydrogels (Mayer et al., Ophthalmologica, 210(2):101-3 (1996)); ophthalmic ointments; ophthalmic suspensions, such as microparticulates, drug-containing small polymeric particles that are suspended in a liquid carrier medium (Joshi, A., J. Ocul. Pharmacol., 10(1):29-45 (1994)), lipid-soluble formulations (Alm et al., Prog. Clin. Biol. Res., 312:447-58 (1989)), and microspheres (Mordenti, Toxicol. Sci., 52(1):101-6 (1999)); and ocular inserts. All of the above-mentioned references are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compound(s) or combination of compounds disclosed herein may also be formulated in rectal compositions such as suppositories or retention enemas, e.g., containing conventional suppository bases such as cocoa butter or other glycerides.

In addition to the formulations described previously, the compound or combination of compounds disclosed herein may also be formulated as a depot preparation. Such long acting formulations may be administered by implantation (for example subcutaneously or intramuscularly) or by intramuscular injection. Thus, for example, the compound or combination of compounds disclosed herein may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compound(s) or combination of compounds disclosed herein or pharmaceutical compositions may be administered to the patient by any suitable means. Non-limiting examples of methods of administration include, among others, (a) administration though oral pathways, which includes administration in capsule, tablet, granule, spray, syrup, or other such forms; (b) administration through non-oral pathways such as rectal, vaginal, intraurethral, intraocular, intranasal, or intraauricular, which includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound or combination of compounds disclosed herein into contact with living tissue.

Pharmaceutical compositions suitable for administration include compositions where the compound(s) or combination of compounds disclosed herein is contained in an amount effective to achieve its intended purpose. The therapeutically effective amount of the compound or combination of compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, and the specific use for which the compound or combination of compounds disclosed herein are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

As used herein, a "dosage" refers to the combined amount of the active ingredients (e.g., L-ornithine and phenylacetate or phenylbutyrate).

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, preferably between about 80 mg/kg and 1600 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compound or combination of compounds disclosed herein may be administered orally or via injection at a dose from 0.1 mg/kg to 4000 mg/kg of the patient's body weight per day. The dose range for adult humans is generally from 1 g to 100 g/day. Tablets or other forms of presentation provided in discrete units may conveniently contain an amount of the compound or combination of compounds disclosed herein which is effective at such dosage or as a multiple of the same, for instance, units containing 1 g to 60 g (for example, from about 5 g to 20 g, from about 10 g to 50 g, from about 20 g to 40 g, or from about 25 g to 35 g). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. A typical dose of ornithine, or of phenylacetate or phenylbutyrate is from 0.02 g to 1.25 g per kg of body weight, for example from 0.1 g to 0.5 g per kg of body weight, depending on such parameters. In some embodiments, a dosage of ornithine, or of phenylacetate or phenylbutyrate can be from 1 g to 100 g, for example, from 10 g to 80 g, from 15 g to 60 g, from 20 g to 40 g, or from 25 g to 35 g. In some embodiments, the ornithine and phenylacetate/phenylbutyrate can be administered in a weight ratio from 10:1 to 1:10, for example, from 5:1 to 1:5, from 4:1 to 1:4, from 3:1 to 1:3, from 2:1 to 1:2, or about 1:1. A physician will be able to determine the required dosage of ornithine and of phenylacetate or phenylbutyrate for any particular subject.

The exact formulation, route of administration and dosage for the pharmaceutical compositions of the compound or combination of compounds disclosed herein can be chosen by the individual physician in view of the patient's condition. (See, e.g., Fingl et al. 1975, in "The Pharmacological Basis of Therapeutics," which is hereby incorporated herein by reference, with particular reference to Ch. 1). Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, the composition is administered 1 to 4 times per day. Alternatively the compositions of the compound or combination of compounds disclosed herein may be administered by continuous intravenous infusion, preferably at a dose of each active ingredient up to 100 g per day. As will be understood by those of skill in the art, in certain situations it may be necessary to administer the compound disclosed herein in amounts that exceed, or even far exceed, the above-stated, preferred dosage range in order to effectively and aggressively treat particularly aggressive diseases or infections. In some embodiments, the compound or combination of compounds disclosed herein will be administered for a period of continuous therapy, for example for a week or more, or for months or years.

In some embodiments, the dosing regimen of the compound(s) or combination of compounds disclosed herein is administered for a period of time, which time period can be, for example, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the compound(s) or combination of compounds disclosed herein can be administered three times a day, twice a day, daily, every other day, three times a week, every other week, three times per month, once monthly, substantially continuously or continuously.

Some embodiments provide a method to use an effective amount of the compound(s) or combination of compounds disclosed herein in the treatment of portal hypertension and/or restoration of liver function in a patient comprising administering to the patient a dosage of the compound(s) or combination of compounds disclosed herein containing an amount of about 1 g to about 100 g of drug per dose of the compound or combination of compounds disclosed herein, orally, three times per month, once monthly, once weekly, once every three days, once every two days, once per day, twice per day, or three times per day substantially continuously or continuously, for the desired duration of treatment.

Some embodiments provide a method to use an effective amount of the compound(s) or combination of compounds disclosed herein in the treatment of portal hypertension and/or restoration of liver function in a patient comprising administering to the patient a dosage of the compound or combination of compounds disclosed herein containing an amount of from 0.1 mg to about 4000 mg of drug per kilogram of body weight per dose of the compound or combination of compounds disclosed herein, orally, three times per month, once monthly, once weekly, once every three days, once every two days, once per day, twice per day, or three times per day substantially continuously or continuously, for the desired duration of treatment.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. In some embodiments, compositions can be administered using a regimen which maintains plasma levels above the MEC for 10-90% of the time, for example, between 15-30%, 20-45%, 25-50%, 30-55%, 35-60%, 40-65%, 45-70%, 50-75%, 55-80%, 60-90%, 65-75%, 70-80%, 75-85%, 15-90%, 20-90%, 25-90%, 30-90%, 35-90%, 40-90%, 45-90%, 50-90%, 55-90%, 60-90%, 65-90%, 70-90%, 75-90%, or 80-90%. In some embodiments, compositions can be administered using a regimen which maintains plasma levels above the MEC for 20-90% of the time. In some embodiments, compositions can be administered using a regimen which maintains plasma levels above the MEC for 30-90% of the time, between 40-90% and most typically between 50-90%.

In cases of local administration or selective uptake, the effective local concentration of the drug may not be related to plasma concentration.

The amount of composition administered may be dependent on the subject being treated, on the subject's weight, the severity of the affliction, the manner of administration and the judgment of the prescribing physician.

The compound(s) or combination of compounds disclosed herein can be evaluated for efficacy and toxicity using known methods. For example, the toxicology of the compound or combination of compounds disclosed herein may be established by determining in vitro toxicity towards a cell line, such as a mammalian, and preferably human, cell line. The results of such studies are often predictive of toxicity in animals, such as mammals, or more specifically, humans. Alternatively, the toxicity of the compound or combination of compounds disclosed herein in an animal model, such as mice, rats, rabbits, or monkeys, may be determined using known methods. The efficacy of the compound or combination of compounds disclosed herein may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising the compound or combination of compounds disclosed herein formulated in a compatible pharmaceutical carrier may also be prepared, placed in an appropriate container, and labeled for treatment of an indicated condition.

An effective amount of the compound(s) or combination of compounds disclosed herein may be determined by one of ordinary skill in the art. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to portal hypertension.

Pharmaceutical compositions comprising the compound(s) or combination of compounds disclosed herein capable of treating portal hypertension in an amount effective therefore, and a pharmaceutically acceptable vehicle or diluent are also disclosed. The compositions of the present disclosure may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compound(s) or combination of compounds disclosed herein may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents.

The compound(s) or combination of compounds disclosed herein, for example, may be administered in a form suitable for immediate release or extended release. Immediate release or extended release may be achieved by the use of suitable pharmaceutical compositions comprising the compound(s) or combination of compounds, or, particularly in the case of extended release, by the use of devices such as subcutaneous implants or osmotic pumps.

The compound(s) or combination of compounds disclosed herein may also be administered liposomally. For example, the active substance can be utilized in a composition such as tablet, capsule, solution or suspension containing the compound or combination of compounds disclosed herein or in topical form for wound healing (0.01 to 5% by weight the compound or combination of compounds disclosed herein, 1 to 5 treatments per day).

The compound(s) or combination of compounds disclosed herein may be compounded in a conventional manner with a physiologically acceptable vehicle or carrier, excipient, binder, preservative, stabilizer, flavor, etc., or with a topical carrier.

The compound(s) or combination of compounds disclosed herein can also be formulated in compositions such as sterile solutions or suspensions for parenteral administration. The compound or combination of compounds disclosed herein may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include those formulating the compound or combination of compounds disclosed herein with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compound or combination of compounds disclosed herein may be administered topically to treat peripheral vascular diseases and as such may be formulated as a cream or ointment.

The compound(s) or combination of compounds disclosed herein may be employed alone or in combination with other suitable therapeutic agents useful in the treatment of portal hypertension or restoration of liver function. For example, the compound or combination of compounds disclosed herein can be administered in combination with vasopressin analogues such as terlipressin, ornipressin and vasopressin; somatostatin and its analogues such as octreotide; non-selective beta blockers such as propranolol and nadolol; vasodilating beta blockers such as carvedilol; nitrates such as isosorbide mono-nitrate and glycerine tr-nitrate; and statins such as Atorvastatin, Fluvastatin, Lovastatin and Simvastatin The above other therapeutic agents, when employed in combination with the compound or combination of compounds disclosed herein, may be used, for example, in those amounts indicated in the Physicians' Desk Reference (PDR) or as otherwise determined by one of ordinary skill in the art.

EXAMPLES

Embodiments of the present application are disclosed in further detail in the following examples, which are not in any way intended to limit the scope of the present disclosure.

Example 1

In this example, experiments were conducted on the clinically relevant, bile duct-ligated (BDL) rat model of cirrhosis, which exhibits clinical characteristics of low-grade systemic and brain proinflammatory state indicated by elevated cytokines such as tumour necrosis factor-alpha (TNF-α)) along with low-grade brain oedema. In BDL rats, administration of bacterial Lipopolysaccharide (LPS) leads to a clinical situation that mimics clinical ACLF.

It has been shown that naive rats exposed to ammonia followed by intravenous LPS, developed an inflammatory response, cerebral vasodilation and intracranial hypertension, which did not occur in animals administered LPS alone, indicating the important role of ammonia in 'priming' the brain to the deleterious effect of LPS. There is an exaggeration of both systemic and brain inflammatory response which results in worsening of the cytotoxic brain oedema resulting in a decline in consciousness to pre-coma/coma stages.

Animal Models

Thirty-four male Sprague-Dawley rats, body weight 200-250 g were used. All rats were housed in the unit and given free access to standard rodent chow and water, with a light/dark cycle of 12 hours, at a temperature of 19-23° C. and humidity of approximately 50%.

Bile Duct-Ligation (BDL):

Rats underwent bile duct-ligation to induce biliary cirrhosis under anesthesia—intravenous (IV) diazepam (1 mg/kg), followed by a 150 μl/kg of intramuscular Hypnorm® (Janssen Pharmaceutica, Belgium).

Sham-Operated (Sham):

Rats underwent sham-operation under anesthesia. BDL rats were administered a high protein/ammoniagenic diet for 7 days prior to inclusion in the study. The diet consisted of a liquid rodent feed (Bioserve, Frenchtown, N.J. 08825, USA) and a tailor-made mixture mimicking the amino-acid composition of haemoglobin molecule (4 g/Kg/day Nutricia, Cuijk, The Netherlands) mixed with commercially available gelatin to prevent sedimentation. This regimen produces chronic hyperammonaemia.

Study Design

The effect of treating superimposed inflammation on the background of hyperammonemia indicative of ACLF was investigated by administering OP. Four weeks after surgery, BDL rats were randomized to receive 3 days of successive intraperitoneal (IP) injections of OP (0.3 g/kg), the mouse chimeric anti-TNF-α monoclonal antibody, or saline (placebo). Three hours before termination, all BDL rats were administered IP—1 mg/kg LPS (Sigma. Poole, UK). As controls, sham-operated rats only received IP saline. Study groups were 1) sham-operated (n=6), 2) BDL+saline (n=6), 3) BDL+LPS (n=6), and 4) BDL+OP+LPS (n=6).

A further study was conducted in order to determine the ammonia-lowering effect of OP on brain inflammatory responses in just BDL (non-LPS treated) rats. Four weeks after surgery, BDL rats were randomised to receive 3 days of successive intraperitoneal (IP) injections of OP (0.3 g/kg) and/or saline (placebo). As controls, sham-operated rats only received IP saline. Study groups were 1) sham-operated (n=6), 2) BDL+saline (n=6) and 3) BDL+OP (n=6). As per protocol, the rats were allowed free access to food and water for the period of 3 hours post-intervention in a temperature controlled environment and were then sacrificed by exsanguination under anesthesia—IP Hypnorm® (200 μL/kg), 20 minutes after IP diazepam (1 mg/kg). Blood was withdrawn from the descending aorta and immediately put into ice cold heparin/EDTA containing tubes (until full exsanguination), centrifuged at 3,120×g and 4° C., and the plasma collected and stored at −80° C. until assayed.

Plasma and Cortical Brain Cytokines

Plasma and cortical brain samples were snap frozen (−80° C.) and stored. Prior to analysis, 100 μg of cerebral cortex was homogenised and deproteinised (using a glass tube Teflon pestle homogeniser) in 300 μl of ice-cold cell lysis buffer solution. After centrifugation at 12,000×g for 10 minutes at 4° C., the supernatants were collected for processing. Following protein concentration quantification of equilibrated brain protein samples and plasma supernatants (50 μl) were analysed for cytokine levels (pg/ml) by flow cytometry using the Becton Dickinson (BD™ biosciences) rat inflammation cytometric bead array (CBA) kit as described by the manufacturer's instructions. These included the proinflammatory cytokines—TNF-α and interleukin-6 (IL-6). Samples were analysed by measuring the fluorescence produced by the CBA beads on an FACS Canto™ II flow cytometry system (BD™ Sciences) and the data analysed with BD™ CTA software.

Western Blot Analysis

Snap frozen (−80° C.) and stored 100 μg cortical brain samples were homogenised and deproteinised (using a glass tube Teflon pestle homogenizer) in 300 μl of ice-cold cell lysis buffer solution. After centrifugation at 12,000 g for 10 minutes at 4° C., the supernatants were collected for processing. Following quantification of sample protein concentration (of equilibrated 50 μl frontal cortical brain tissue), western-blot was performed on prepared samples for protein separation and transfer using a NuPAGE® pre-cast gel system (Invitrogen Ltd, UK). Specific protein bands were detected using an iNOS mouse primary (BD Biosciences, UK) and secondary goat polyclonal antibody to mouse IgG, HRP conjugated (Hycult biotechnology, Netherlands), and p65 NFkB—rabbit primary (cell signalling, UK) with a secondary goat polyclonal antibody to rabbit IgG, HRP conjugated (Hycult biotechnology, Netherlands). Antibody to alpha-tubulin (α-tubulin; Santa Cruz Biotechnology, Inc. USA), a ubiquitous cellular cytoskeletal protein, was measured to establish accurate differences in total protein expression between sample tissues; requiring a secondary goat polyclonal antibody to mouse IgG, HRP conjugated (Hycult biotechnology, Netherlands) for detection. All antibodies were used at a dilution of 1:1000. Protein bands were visualized using Amersham ECL™ advance western blotting detection reagents and Hyperfilm™ (GE Healthcare, UK). Densitometry measurements where made using Image-J software (freeware; rsbweb.nih.gov/ij).

Statistics

Data are expressed as mean±SEM. Significance of difference was tested with Newman-Keuls multiple comparison test or two-way ANOVA; $p<0.05$ was taken to be statistically significant. Paired t test or Wilcoxon Signed Rank test was used for comparison of two groups as appropriate. Kaplan-Meier survival analyses were performed for the time to pre-coma/coma in the different treatment groups and the log-rank test was used for statistical analysis of the data comparing the survival curves. Software used included Microsoft Excel 2003 (Microsoft Corp., Redmond, Wash.) and GraphPad Prism 4.0 (GraphPad Software, Inc., San Diego, Calif.).

of TNF-α ($p>0.05$, Table 1), which was augmented by LPS ($p<0.001$). In LPS treated BDL rats, administration of OP ameliorated the elevated cortical TNF-α brain tissue levels ($p<0.05$). There was a similar trend with brain IL-6 levels following bile duct-ligation and treatment intervention.

Plasma and Cortical Brain Cytokines

Plasma Cytokines:

When compared to sham-operated rats (114.8±40.4 pg/ml), BDL was associated with a significant increase in the plasma levels of TNF-α (902.2±176.1 pg/ml; $p<0.001$), which were significantly reduced by pre-treatment with OP (270.5±59.4 pg/ml; $p<0.001$).

Cortical Brain Cytokines:

When compared to sham-operated rats (34.2±4.6 pg/ml), BDL was associated with a significant increase in the brain levels of TNF-α (178.7±62.9 pg/ml; $p<0.05$), which were significantly reduced by pre-treatment with OP (54.7±15.3 pg/ml; $p<0.05$).

iNOS Expression

When compared to sham-operated rats (1.46±0.17; FIG. 2A), there was a significant rise in brain iNOS with BDL (2.87±0.14; $p<0.001$), which was reduced following pre-treatment with OP (2.32±0.17; $p<0.05$).

NFκB Expression

TABLE 1

| Cytokine levels (pmol/L) | Sham | BDL | BDL + LPS | BDL + OP + LPS |
|---|---|---|---|---|
| Plasma TNF-a | 90 ± 25 | 1859 ± 417* | 4143 ± 528*** | 1919 ± 828$^{\$\$}$ |
| Plasma IL-6 | 153 ± 52 | 1470 ± 422 | 4135 ± 560***/## | 3730 ± 832 |
| Brain TNF-a | 45 ± 13 | 237 ± 79* | 402 ± 57*** | 165 ± 12$^{\$}$ |
| Brain IL-6 | 26 ± 5 | 144 ± 99 | 285 ± 104 | 126 ± 84 |

Data are expressed as mean ± standard error of mean (SEM) Symbols represent;-
*$p < 0.05$ and
***$p < 0.001$ compared to sham-operated control rats;
$^{\$}p < 0.05$ and
$^{\$\$}p < 0.01$ compared to BDL + LPS rats and
$^{\#\#}p < 0.01$ compared to BDL rats.
Abbreviations: sham, sham-operated. BDL, bile duct-ligation. LPS, lipopolysaccharide.

Results

All rats continued to gain weight following surgery. From the final weight taken immediately prior to termination, BDL rats (mean±SEM; 342 g±42) were not significantly different to sham-operated controls (mean±SEM; 380 g±38). The systemic haemodynamics in the BDL animals were well maintained as previously shown.

Plasma and Cortical Brain Cytokines

Throughout all study groups, the mean frontal cortical brain tissue cytokine levels were in the order of 10 fold higher compared to their respective circulating plasma levels (FIG. 1A-D and Table 1). Multiple comparison group analysis revealed the following:

Plasma Cytokines:

When compared to sham-operated rats, bile duct-ligation was associated with a significant increase in the plasma levels of the proinflammatory cytokines TNF-α ($p<0.05$) (FIG. 1A). In BDL rats, LPS challenge significantly increased plasma TNF-α and IL-6 when compared to sham-operated controls ($p<0.001$, respectively) and saline-treated BDL controls ($p<0.01$, respectively) (FIGS. 1B-C). When compared to BDL+LPS rats, there was a significant reduction in plasma TNF-α ($p<0.01$) and trend towards reduction in IL-6 following administration of OP (FIGS. 1B-D).

Cortical Brain Cytokines:

When compared to sham-operated rats, bile duct-ligation was associated with a significant increase in the brain levels When compared to sham-operated rats (2.65±0.17; FIG. 2B), there was a significant rise in brain NFκB with BDL (4.25±0.13; $p<0.001$), which was markedly reduced following pre-treatment with OP (2.52±0.19; $p<0.001$).

In this example, BDL rats for 4-weeks prior to the study represents chronic liver disease with hyperammonaemia and a proinflammatory state indicated by elevated arterial and brain cytokines. Additionally, the administration of LPS to this model is reflective of a second hit, and in this context represents an infective episode with evidence of exaggeration of the inflammatory response manifested by an increase in TNF-α and IL-6. The cirrhotic brain exhibits classical 'cytotoxic oedema' even in the LPS treated group. Ammonia and inflammation work simultaneously (and in synergy) to produce brain oedema and coma.

It was observed that OP treatment was associated with a reduction in plasma and brain proinflammatory cytokines as well.

Modulation of Brain eNOS Activity

Example 2

Asymmetric dimethylarginine (ADMA) is an endogenous inhibitor of eNOS, the levels of which are increased in liver failure. A study was conducted to determine whether administration of combinations of L-ornithine and phenylacetate impacts upon the NO pathway. This example addresses the questions: (a) is eNOS activity reduced in cirrhotic brains? (b) is ADMA level increased and di-hydro diamino hydrolase (DDAH, enzyme that breaks down ADMA) decreased in cirrhotic brains: (c) are other regulators of eNOS activity altered in cirrhotic brains, and whether these are restored by L-ornithine in combination with phenylacetate (OP)?

Sprague-Dawley rats were studied 4-weeks after bile duct ligation (BDL) (n=16) or sham operation (n=8) and randomized to treatment with placebo or OP (0.6 gm/kg) i.p. Arterial blood, frontal brain tissue and urine were collected at the time of sacrifice. Ammonia and amino-acids were measured in the plasma using Cobas-MiraS and HPLC respectively. Brain water was measured using the dry weight technique. Urinary phenylacetyglutamine and plasma and brain ADMA were measured using LCMS. eNOS activity was measured using radiolabelled $^1H$ Arginine and protein expression for eNOS, DDAH-1 and Caveolin measured using Western Blotting.

Treatment of BDL rats with OP resulted in normalization of arterial ammonia ($p<0.001$), brain water ($p<0.001$) and increased urinary phenylacetylglutamine ($p<0.01$). eNOS activity was significantly lower but eNOS protein expression was greater in BDL animals compared with sham operated controls which was restored towards sham values in the OP treated animals. Brain ADMA levels were significantly higher in BDL compared with sham and brain DDAH-1 was significantly lower which was restored on treatment with OP. Brain Caveolin was significantly lower in BDL animals, which was increased towards sham values in the OP treated animals.

This example showed that the brain nitric oxide pathway is adversely affected by hyperammonemia, which can be restored by treatment with OP. These results demonstrated that OP may be used for the treatment of organ systems in cirrhosis that are known to have deranged NO signalling.

Example 3

Sham operated Sprague-Dawley rats (n=10) and BDL rats (n=10) were compared four weeks after BDL surgery, and in an additional BDL group (n=6), after administration of 3 g/kg i.p. OP twice a day for 5 days. Ammonia and amino-acids were measured in the plasma using Cobas-Integra and HPLC, respectively. Brain water was measured using the dry weight technique. TNFα was measured by FACS bead array. Urinary phenylacetylglutamine and plasma and brain ADMA were measured using LC-MS/MS-respectively. eNOS and DDAH activity was measured radiometrically. Protein expression for eNOS, DDAH-1&2 and caveolin-1 were measured by western blotting.

As shown below, plasma (FIG. 3A) and brain (FIG. 3B) TNF-α levels were significantly elevated in BDL rats compared to sham ($p<0.01$, for both). OP treatment reverts these changes near to sham and are significant when compared to BDL alone ($p<0.05$; $p<0.01$, respectively).

As shown in FIG. 4, eNOS activity (FIG. 4A) was significantly decreased in BDL rat brain compared to sham despite increased eNOS protein expression (FIG. 4B). Following treatment with OP, eNOS activity reverted to sham levels, with similar normalization of eNOS protein expression. iNOS protein was also significantly elevated in BDL rat (FIG. 4C). OP treatment significantly down regulated iNOS protein as compared to BDL alone (FIG. 4C).

As shown in FIG. 5, plasma ADMA (FIG. 5A) was significantly elevated in BDL rat plasma ($p<0.01$) and brain homogenates (FIG. 5B) ($p<0.05$) compared with sham. Following OP treatment, there was a non-significant reduction in plasma ADMA but a significant reduction in brain ADMA concentration as compared to BDL. Moreover, cerebral caveolin-1 protein expression (FIG. 5C) was increased significantly in BDL rat compared to sham ($p<0.01$). Treatment with OP reverted caveolin-1 protein to sham levels ($p<0.05$).

As shown in FIG. 6, cerebral DDAH-1 (FIG. 6A) protein expression was decreased significantly ($p<0.05$) in BDL rat. Conversely, cerebral DDAH-2 (FIG. 6B) protein expression was significantly elevated ($p<0.05$) compared to sham. Following OP administration, DDAH-1 increased significantly ($p<0.05$) and DDAH-2 protein expression decreased significantly ($p<0.05$) compared to BDL. Moreover, DDAH activity (FIG. 6C) was significantly elevated in BDL rat brain compared to sham. OP treatment significantly ($p<0.01$) decreased DDAH activity as compared to BDL alone ($p<0.01$).

Modulation of Liver eNOS Activity

Example 4

In cirrhosis, portal hypertension is associated with hepatic inflammation which contributes to reduced intrahepatic endothelial nitric oxide synthase (eNOS) activity, which is associated with the increased endogenous NOS inhibitors, Caveolin-1 and asymmetric-dimethylarginine (ADMA). This example is to determine whether treatment with L-ornithine phenylacetate combinations (OP) reduces NFκB and increases intrahepatic NO availability through modulation of these inflammatory dependent inhibitors of endothelial NOS and thereby reduces portal pressure.

Sprague-Dawley rats were studied 4-weeks after BDL surgery (n=16) or sham operation (n=8) and randomized to treatment with placebo or OP (0.6 gm/kg) i.p. for 5 days prior to study. Rats underwent direct portal pressure measurement under anaesthesia at the time of sacrifice and plasma and liver tissue was harvested for subsequent analysis. Plasma ammonia and biochemistry were measured using a Cobas-MiraS analyser, and eNOS activity was determined radiometrically. Protein expression for eNOS, DDAH-1, Caveolin-1, and NFkB were measured using Western Blotting.

Treatment with OP resulted in a reduction in hyperammonaemia ($p<0.001$) towards sham values and an increase in hepatic eNOS activity towards sham levels. This was associated with a significant reduction in portal pressure compared with placebo treated group (11±0.4 vs. 14±0.7 mmHg, $p=0.01$). Moreover, OP treatment significantly reduced the expression of Caveolin-1 ($p<0.05$) and increased expression of dimethylarginine-dimethylamainohydrolase-1 ($p<0.05$) [DDAH 1 is responsible for metabolism of ADMA], whilst also significantly lowering hepatic phosphorylated NFkB expression, compared with placebo treated animals.

This example showed that treatment of hyperammonemia with OP reduces the severity of portal hypertension in a clinically relevant model of cirrhosis through restoration of the hepatic eNOS activity by modulating NFκB and the expression of eNOS regulators, DDAH1-ADMA and Caveolin-1.

Example 5

Four weeks after BDL and sham surgery in Sprague-Dawley rats, BDL rats were given i.p. OP 3 g/kg twice a day or vehicle alone (n=14/group), and treated for 5 days. After the 5th treatment day, all rats underwent direct portal pressure measurement under anaesthesia prior to sacrifice. Plasma and liver tissue was harvested for subsequent analysis. Plasma ammonia and biochemistry were measured using a Cobas-Integra analyzer. Plasma TNFα was measured by FACS bead array. eNOS activity was determined radiometrically. Protein expression for eNOS, DDAH-1, caveolin-1, and NFkB were measured using standard Western Blotting techniques.

Effect of OP on arterial ammonia and plasma biochemistry of BDL rats is indicated in Table 2. Statistical significance was calculated using student t' test Mann Witney comparisons test. *—P<0.01 versus sham; **—P<0.001 versus sham; †—P<0.01 versus BDL; § —P<0.05 versus BDL; NS—no significance.

TABLE 2

| Parameters | Sham | BDL | BDL + OP |
|---|---|---|---|
| Ammonia (μmol/L) | 55.86 ± 4.05 | 222.3 ± 24.01** | 127.1 ± 47.8† |
| ALT (U/L) | 26.88 ± 2.61 | 159.8 ± 10.81** | 108.3 ± 5.66† |
| Bilirubin (μmol/L) | 32.52 ± 2.43 | 304.9 ± 25.97** | 267.7 ± 14.5NS |
| Creatinine (μmol/L) | 23.07 ± 0.94 | 40.88 ± 2.37* | 32.38 ± 1.44§ |
| TNF-α (pg/ml) | 121.9 ± 46.4 | 822.9 ± 203.1* | 270.5 ± 59.4§ |

As shown in FIGS. 7A and 7B, eNOS activity was significantly decreased in BDL animals compared to sham (p<0.05) despite increased eNOS protein expression (p<0.01). Following treatment with OP, eNOS activity reverted to sham levels, with similar normalisation of eNOS protein expression (p<0.05). As shown in FIG. 7C, DDAH-1 protein expression was significantly higher in sham animals compared to BDL (p<0.01). Following OP administration to BDL rats, DDAH-1 expression increases significantly and reverts to sham levels (p<0.05). As shown in FIG. 7D, protein expression of NFkB was significantly elevated in BDL rats compared to sham (p<0.01). OP treatment produces a marked reduction in NFkB expression compared to BDL (p=0.05). As shown in FIG. 7E, the expression of caveolin-1 was significantly elevated in BDL rats compared to sham (p<0.01). Following intervention with OP, Caveolin-1 expression decreased significantly (p<0.05) compared to BDL alone. As shown in FIG. 7C, portal pressure was significantly increased in BDL rats compared to sham (p<0.0001). OP treatment results in a 30% reduction of portal pressure as compared to BDL (P<0.01).

Example 6

This example is to determine whether treatment with L-ornithine phenylacetate combinations (OP) improves liver function (e.g., perfusion).

Sprague-Dawley rats are studied 4-weeks after bile duct ligation (BDL) and randomized to treatment with placebo or OP. The liver function of the BDL rats is measured by a variety of methods. For example, liver injury is detected by the alanine transaminase (ALT) test, aspartate aminotransferase (AST) test, and/or alpha glutathione S-transferase (GST) test. Liver function is measured by albumin (Alb) test; prothrombin time test; and/or composite scores, such as child-pugh score' MELD score. Liver hemodynamics is measured by detecting liver blood flow and/or portal pressure.

The administration of OP is effective in improving and/or restoring liver function, e.g., increasing liver perfusion, in the BDL rats. OP treatment is also effective in reducing portal pressure in the BDL rats.

Example 7

This example is to determine whether treatment with L-ornithine phenylacetate combinations (OP) decreases variceal bleeding in BDL rats with portal hypertension.

Sprague-Dawley rats are studied 4-weeks after bile duct ligation (BDL) and randomized to treatment with placebo or OP. Portal pressure of the BDL rats is measured. The BDL rats are also detected for variceal bleeding and the extent of variceal bleeding of the BDL rats is measured.

The administration of OP is effective in reducing portal pressure and decreasing variceal bleeding in the BDL rats.

Example 8

This example is to determine whether treatment with L-ornithine phenylacetate combinations (OP) decreases ascites in BDL rats with portal hypertension.

Sprague-Dawley rats are studied 4-weeks after bile duct ligation (BDL) and randomized to treatment with placebo or OP. Portal pressure of the BDL rats is measured. The BDL rats are also detected for ascites and the extent of ascites of the BDL rats is measured.

The administration of OP is effective in reducing portal pressure and ascites in the BDL rats.

Although the present disclosure has been described with reference to embodiments and examples, it should be understood that numerous and various modifications can be made without departing from the spirit of the present disclosure. Accordingly, the present disclosure is limited only by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of reducing portal pressure in a subject, comprising:
   identifying a subject that is in need of reducing portal pressure, wherein the subject has a condition selected from the group consisting of portal hypertension, portal hypertension related variceal bleeding, and portal hypertension related ascites;
   administering to the subject L-ornithine in combination with at least one of phenylacetate and phenylbutyrate or a physiological acceptable salt of at least one of phenylacetate and phenylbutyrate, wherein the L-ornithine is present as a free monomeric amino acid or physiologically acceptable salt thereof; and
   measuring the portal pressure of the subject that has been administered with the L-ornithine in combination with at least one of phenylacetate and phenylbutyrate or the physiological acceptable salt of at least one of phenylacetate and phenylbutyrate to determine the reduction in portal pressure in the subject;
   wherein the reduction in portal pressure in the subject is at least 30%.

2. The method of claim 1, wherein the subject is suffering from a liver disease.

3. The method of claim 2, wherein the liver disease is a chronic liver disease or an acute liver failure.

4. The method of claim 3, wherein the chronic liver disease is cirrhosis.

5. The method of claim 1, wherein the reduction in portal pressure is achieved by reducing the level of proinflammatory cytokines or increasing endothelial nitric oxide synthase activity in the subject.

6. The method of claim 1, wherein said L-ornithine and phenylacetate are administered as L-ornithine phenyl acetate.

7. The method of claim 1, wherein separate physiologically acceptable salts of said L-ornithine and at least one of phenylacetate and phenylbutyrate are administered to the subject.

8. The method of claim 1, wherein at least one of phenylacetate and phenylbutyrate is administered as a sodium phenylacetate or sodium phenylbutyrate.

9. The method of claim 1, wherein said administration is oral, intravenous, intraperitoneal, intragastric, or intravascular administration.

10. The method of claim 1, wherein the dose of the L-ornithine and the phenylacetate or phenylbutyrate administered is between 20 g and 40 g.

11. A method of delaying or reducing the likelihood of onset of portal hypertension in a subject, comprising:
    administering to the subject L-ornithine in combination with at least one of phenylacetate and phenylbutyrate or a physiological acceptable salt of at least one of phenylacetate and phenylbutyrate, wherein the L-ornithine is present as a free monomeric amino acid or physiologically acceptable salt thereof;
    measuring the portal pressure of the subject that has been administered with the L-ornithine in combination with at least one of phenylacetate and phenylbutyrate or the physiological acceptable salt of at least one of phenylacetate and phenylbutyrate, thereby delaying or reducing the likelihood of onset of portal hypertension.

12. The method of claim 11, wherein the subject is suffering from liver disease.

13. The method of claim 11, wherein the delay or reduction in the likelihood of onset of portal hypertension is achieved by reducing the level of proinflammatory cytokines or increasing endothelial nitric oxide synthase activity in the subject.

14. The method of claim 11, wherein said L-ornithine and phenylacetate are administered as L-ornithine phenyl acetate.

15. The method of claim 11, wherein separate physiologically acceptable salts of said L-ornithine and at least one of phenylacetate and phenylbutyrate are administered to the subject.

16. The method of claim 11, wherein at least one of phenylacetate and phenylbutyrate is administered as a sodium phenylacetate or sodium phenylbutyrate.

17. The method of claim 11, wherein said administration is oral, intravenous, intraperitoneal, intragastric, or intravascular administration.

* * * * *